(12) United States Patent
Urban et al.

(10) Patent No.: US 6,207,690 B1
(45) Date of Patent: Mar. 27, 2001

(54) TROGLITAZONE COMPOUNDS FOR TREATING CLIMACTERIC AND CANCER

(75) Inventors: Randall J. Urban, Friendswood, TX (US); Allan Green, Cooperstown, NY (US)

(73) Assignee: Board of Regents, The University Texas System, Austin, TX (US)

( * ) Notice: Subject to any disclaimer, the term of this patent is extended or adjusted under 35 U.S.C. 154(b) by 0 days.

(21) Appl. No.: 09/389,828

(22) Filed: Sep. 3, 1999

Related U.S. Application Data

(63) Continuation of application No. PCT/US98/04061, filed on Mar. 3, 1998, which is a continuation-in-part of application No. 08/811,419, filed on Mar. 4, 1997, now Pat. No. 5,814,674.

(51) Int. Cl.$^7$ .................................................. A61K 31/44
(52) U.S. Cl. .......................... 514/369; 514/252; 514/256; 514/342; 514/360; 514/375; 514/376
(58) Field of Search .................................... 514/369, 252, 514/256, 342, 360, 375, 376

(56) References Cited

U.S. PATENT DOCUMENTS

| | | | |
|---|---|---|---|
| 4,340,605 | 7/1982 | Kawamatsu et al. | 424/263 |
| 5,478,852 | * 12/1995 | Olefsky et al. | 514/369 |
| 5,814,647 | 9/1998 | Urban et al. | 514/369 |

FOREIGN PATENT DOCUMENTS

| | | |
|---|---|---|
| WO 92/07838 | 5/1992 | (WO) . |
| WO 97/00249 | 1/1997 | (WO) . |
| WO 98/25598 | 6/1998 | (WO) . |

OTHER PUBLICATIONS

Mueller et al., "Terminal differentiation of human breast Cancer through PPARγ," *Molecular Cell*, 1:465–470, Feb. 1998.

In: *The Merck Encyclopdia: An Encyclopedia of Chemicals, Drugs and Biologicals*, 12$^{th}$ ed., p. 1282, entry 7605 "Pioglitazone," 1996.

Barentsen R, Eur J Obs Gyn & Repr Biol 64 Suppl:s7–11, 1996.

Berge et al., "Pharmaceutical Salts," *J. Pharm. Science*, 66:1–19, 1977.

Calabresi and Chabner, *Chemotherapy of Neoplastic Diseases*, pp. 1202–1208.

Connelly and Budd, Seminars in Oncology 23:16–21, 1996.

Dunaif et al., "The insulin–sensitizing agent Troglitazone improves metabolic and reproductive abnormalities in the polycystic ovary syndrome," *J. Clin. Endocrinol. Metab.*, 81:3299–3306, 1996.

*Estrogens and Progestins*, Chapter 58, pp. 1392–1412.

Forman et al., "15–Deoxy–delta$^{12, 14}$–Prostaglandin J$_2$ is a ligand for the adipocyte determination factor PPAR gamma," *Cell*, 83:803–812, 1995.

Iwamoto et al., "Effects of Troglitazone: A New Hypoglycemic Agent in Patients with NIDDM Poorly Controlled by Diet Therapy," Diabetes Care, 19(2):151–156, 1996.

Kellerer et al., "Troglitazone Prevents Glucose–Induced Insulin Resistance of Insulin Receptor in Rat–1 Fibroblasts," Diabetes, 43:447–453, 1994.

Kliewer et al., "A prostaglandin J$_2$ metabolite binds peroxisome proliferator–activated receptor gamma and promotes adipocyte differentiation," *Cell*, 83:813–819, 1995.

Lehmann et al., "An antidiabetic thiazolidinedione is a high affinity ligand for peroxisome proliferator–activated receptor gamma (PPARgamma)," *J. Biol. Chem.*, 270:12953–12956, 1995.

Marcus et al., "Identification of COUP–TFII as a peroxisome proliferator response element binding factor using genetic selection in yeast: COUP–TFII activates transcription in yeast but antagonizes PPAR signaling in mammalian cell," *Mol. Cell. Endocrinol.*, 120:31–39, 1996.

Miller, "Molecular biology of steroid hormone synthesis," *Endocr. Rev.*, 9:295–318, 1988.

Motojima, "Peroxisome proliferator–activated receptor (PPAR): Structure, mechanisms of activation and diverse functions," *Cell Structure and Function*, 18:267–277, 1993.

Nolan et al., "Improvement in glucose tolerance and insulin resistance in obese subjects treated with Troglitazone," *N. Engl. J. Med.*, 331:1188–1193, 1994.

Odell, Journal of Otolaryngology 25:7–13, 1996.

Pierce and Figlin RA, Curr Opin Oncology 5:343–352, 1992.

Rainey et al., "Transformation of human granulosa cells with the E6 and E7 regions of human papillomavirus," *J. Clin. Endocrinol. Metabl.*, 78:705–710, 1994.

Shmookler et al., "Giant Cell Fibroblastoma : A Juvenile Form of Dermatofibrosarcoma Protuberans," *Cancer*, 64:2154–2161, 1989.

Shaaban, "The perimenopause and contratception" Maturitas 23:181–192, 1996.

(List continued on next page.)

*Primary Examiner*—James H. Reamer
(74) *Attorney, Agent, or Firm*—Fulbright & Jaworski L.L.P

(57) ABSTRACT

The present invention is directed toward the use of the drug Troglitazone and related thiazolidinedione compounds in the treatment of the climacteric and cancer. This use is based on the novel discovery that Troglitazone inhibits steroidogenesis in granulosa cell cultures. This activity is believed to result from the ability of thiazolidinedione derivatives to act as a ligand for the orphan steroid receptor peroxisome proliferator-activated receptor gamma (PPARγ). Troglitazone and related compounds can therefore be used to prevent excessive uterine bleeding during. Further, enhanced translocation of this orphan nuclear receptor into the nucleus of cells will block transcription in rapidly proliferating cancer cells that express PPARγ, resulting in loss of cell viability.

26 Claims, 12 Drawing Sheets

OTHER PUBLICATIONS

Sutter et al., "Metabolic Effects of New Oral Hypoglycemic Agent CS–045 in NIDDM Subjects," *Diabetes Care*, 15(2):193–202, 1992.

Tontonoz et al., "Terminal Differentiation of Human Liposarcoma Cells Induced by Ligands for Peroxisome Proliferator–Activated Receptor • and the Retinoid X Receptor," *Proc. Natl. Acad. Sci. USA*, 94:237–241, 1997.

Urban et al., "Dexamethasone potentiates IGF–I actions in porcine granulosa cells," *Am. J. Physiol.*, 267:E115–E123, 1994.

Urban et al., "Insulin–like growth factor type I increases concentrations of messenger RNA encoding cytochrome P450 cholesterol side chain cleavage enzyme in primary cultures of porcine granulosa cells," *Endocrinology*, 127:2481–2488, 1990.

Veldhuis and Furlanette, "Trophic actions of human somatomedin C/insulin–like growth factor I on ovarian cells: in vitro studies with swine granulosa cells," *Endocrinology*, 116:1235–1242, 1985.

Vidal–Puig et al., "Regulation of PPAR gamma gene expression by nutrition and obesity in rodents," *J. Clin. Invest.*, 97:2553–2561, 1996.

* cited by examiner

L   B   T

TROGLITAZONE COMPOUNDS FOR TREATING CLIMACTERIC AND CANCER

This is a continuation of co-pending international application number PCT/US98/04061 filed Mar. 3, 1998, which is a continuation-in-part of U.S. patent application Ser. No. 08/811,419 filed Mar. 4, 1997, which issued as U.S. Pat. No. 5,814,674 on Sep. 29, 1998.

The Federal government has rights in the present invention insofar as it was supported by NIH grant No. 1-R01-HD28393.

DESCRIPTION

BACKGROUND OF THE INVENTION

1. Field of the Invention

The present invention relates generally to a novel use of Troglitazone and related thiazolidinedione derivatives. More specifically, it relates to the use of Troglitazone and related thiazolidinedione derivatives in the treatment of the climacteric. It also relates to the use of Troglitazone and the like for the treatment of cancer.

2. Description of Related Art

Troglitazone is a member of a class of antidiabetic drugs termed thiazolidinediones. Although the mechanism is unknown, this class of drugs lowers insulin resistance and improves glucose tolerance(Nolan el al., 1994). For these reasons Troglitazone has found use in the treatment of noninsulin-dependent diabetes mellitus (NIDDM) (U.S. Pat. No. 5,478,852 incorporated by reference herein). NIDDM, otherwise referred to as Type 11 diabetes, is the form of diabetes mellitus which occurs predominately in adults in whom adequate production of insulin is available for use, yet a defect exists in insulin-mediated utilization and metabolism of glucose in peripheral tissues. The population with impaired glucose tolerance progresses to NIDDM at a rate of 5% to 10% of cases per year. Failure to treat NIDDM can result in mortality due to cardiovascular disease and other diabetic complications including retinopathy, nephropathy, and peripheral neuropathy. Administration of Troglitazone can provide effective treatment of populations experiencing impaired glucose tolerance and may result in the delay or prevention of the onset of NIDDM.

Moreover, Troglitazone has been further implicated in the treatment of polycystic ovary syndrome (PCO). This is a syndrome in women that is characterized by chronic anovulation and hyperandrogenism. Women with this syndrome often have insulin resistance and an increased risk for the development of noninsulin-dependent diabetes mellitus. In women with PCO given Troglitazone (400 mg every day), insulin resistance was reduced and 2 of the 25 women studied had ovulatory menses (Dunaif et al., 1996).

While advances continue to be made in chemotherapy treatment of cancer, effective agents are still lacking for the treatment many types of cancer. One such type is mesenchymal tumors. The mesenchyma consists of the meshwork of embryogenic connective tissue in the mesoderm from which are formed the connective tissues of the body as well as blood vessels and lymphatic vessels. There are many types of mesenchymal tumors including but not limited to sarcomas (general), rhabdomyosarcomas, fibrosarcomas, retinoblastoma, hemangiopericytoma, congenital mesoblastic nephroma, and mesotheliomas (Pierce and Figlin, 1992; Odell, 1996; Connelly and Budd, 1996). These types of tumors are aggressive and fast growing, thus development of effective chemotherapeutic agents for their treatment is of particular need.

One mechanism through which thiazolidinediones are believed to have biological effect is their ability to serve as a high affinity ligand for the orphan steroid receptor peroxisome proliferator-activated receptor gamma (PPARγ) (Lehmann et al., 1995). PPARγ is a member of the nuclear receptor superfamily of orphan steroid receptors that serve as transcription factors (Motojima, 1993). This family includes receptors for the steroid, thyroid and retinoid hormones. Activation of PPARγ is implicated in adipocyte differentiation through the activation of adipocyte-specific gene expression (Lehmann et al., 1995). This gene expression is mediated through binding to a PPARγ response element (PPRE) in the promoter region of target genes (Forman et al., 1995). This PPRE is composed of a directly repeating core site separated by one nucleotide (NNN-AGGTCA-N-AGGTCA) (SEQ ID NO:1). To bind to a PPRE, PPARγ must form a heterodimer with the 9-cis retinoic acid receptor (RXR). This sequence is classified as a DR-1 consensus sequence that is universal for orphan receptors (Vidal-Puig, 1996). Because of the universal nature of this consensus sequence, other transcription factors can bind to the PPRE and compete with the binding of PPARγ. One such transcription factor is COUP-TFII that antagonizes PPAR signaling in mammalian cells (Marcus et al., 1996).

PPARγ is in a family of three orphan receptors that are encoded by different genes (Motojima, 1993). The three PPAR genes are PPARα, PPARδ, and PPARγ (Motojima, 1993). Moreover, 2 isoforms of PPARγ also exist, PPARγ1 and γ2 (Vidal-Puig et al., 1996). These 2 proteins differ only in their NH$_2$-terminal-30 amino acids and are the result of alternative promoter usage and differential mRNA splicing (Vidal-Puig et al., 1996). In addition to thiazolidinediones, another ligand for the PPARγ nuclear receptor is the arachidonic acid metabolite 15-deoxy-delta$^{12, 14}$-prostaglandin J$_2$ (15d-PGJ$_2$). This prostaglandin activates PPARγ-dependent adipogenesis, but activated PPARα only at high concentrations (Forman et al., 1995; Kliewer et al., 1995). This is further evidence that the PPAR family subtypes are distinct from one another in their pharmacological response to ligands.

The climacteric is defined as the syndrome of endocrine, somatic and psychological changes occurring at the termination of the reproductive period in the female. The menstrual irregularities are episodes of prolonged menstrual bleeding caused by a loss of ovulation. The loss of ovulation is caused by a failure of development of ovarian follicles. Currently the most common method for treatment of the climacteric is hormone replacement, including administration of birth control pills, oral administration of estrogen and progesterone preparations or oral administration of progesterone only preparations (Shaaban, 1996). While relieving symptoms of the climacteric, these treatments have many associated risks and side effects. Risks associated with hormone treatment include endometrial carcinoma, hypertension, hyperlipidemia, cholelithiasis (gallstones), breast cancer, and deep venous thrombosis (Barentsen, 1996).

Compounds useful for practicing the present invention, and methods of making these compounds are known. Some of these compounds are disclosed in WO 91/07107; WO 92/02520; WO 94/01433; WO 89/08651; JP Kokai 69383/92; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; and 5,260,445. The disclosure of these publications are incorporated herein by reference in particular with respect to the active compounds disclosed therein, and methods of preparation thereof.

SUMMARY OF THE INVENTION

The present invention is the result of the surprising finding that Troglitazone and related thiazolidinedione compounds inhibit steroidogenesis in granulosa cells. A related aspect of the present invention is the discovery that therapeutic levels of Troglitazone can kill rapidly growing cancerous cells expressing the orphan nuclear receptor PPARγ, while not affecting the viability of normal cells. The discovery of these new uses for Troglitazone and related compounds provides important new agents for the treatment of certain types of cancers and for the treatment of the climacteric. The term climacteric is well known in the art as the syndrome of endocrine, somatic and psychological changes occurring at the termination of the reproductive period in the female.

A type of cancer which is particularly likely to be treatable with troglitazone and related thiazolidinedione derivatives are mesenchymal tumors. The mesenchyma consists of the meshwork of embryogenic connective tissue in the mesoderm from which are formed the connective tissues of the body as well as blood vessels and lymphatic vessels. There are many types of mesenchymal tumors including but not limited to sarcomas (general), rhabdomyosarcomas, fibrosarcomas, retinoblastoma, hemangiopericytoma, congenital mesoblastic nephroma, and mesotheliomas.

Studies show that Troglitazone is a ligand for the orphan nuclear receptor PPARγ. Translocation of this transcription factor in the nucleus of cells at sufficient rates inhibits transcription and reduces progesterone production in normal granulosa cells without a loss in cell viability. However, this inhibition of transcription in rapidly dividing cancer cells expressing PPARγ results in the loss of cell viability and inhibition of cell growth. The mechanism of PPARγ inhibition of gene transcription most likely results from the competition of the PPARγ transcription factor with the other orphan nuclear factors binding to DR-1 consensus elements on genes and impairing the promoter activity of those elements. The inhibitory effects of Troglitazone on steroidogenesis make it useful for the reduction of menstrual bleeding in women as they develop reduced ovulation as they approach menopause. Because there is no loss of viability in normal cells, but a reduction in rapidly growing cancer cells, Troglitazone and related compounds may also be used in the treatment of cancer, to impair the growth of cancer cells without killing normal cells As agents having the aforementioned effects, the compounds of the following formulas are useful in treating individuals.

Accordingly, the present invention is the use of compounds of Formula I

Formula I

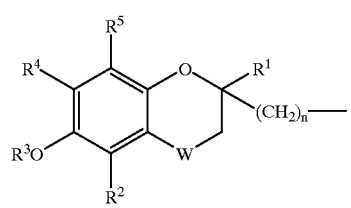

-continued

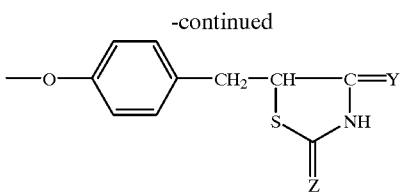

wherein $R^1$ and $R^2$ are the same or different and each represents a hydrogen atom or a $C_1$–$C_5$ alkyl group;

$R^3$ represents a hydrogen atom, a $C_1$–$C_6$ aliphatic acyl group, an alicyclic acyl group, an aromatic acyl group, a heterocyclic acyl group, an aralphatic acyl group, a ($C_1$–$C_6$ alkoxy)carbonyl group, or an aralkyloxycarbonyl group;

$R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_5$ alkylenedioxy group;

n is 1, 2 or 3;

W represents the —$CH_2$—, >CO, or CH—$OR^6$ group (in which $R^6$ represents any one of the atoms or groups defined for $R^3$ and may be the same as or different from $R^3$); and Y and Z are the same or different and each represents an oxygen atom or an imino (=NH) group; and pharmaceutically acceptable salts thereof.

The present invention is also the use of compounds of the Formula II

Formula II

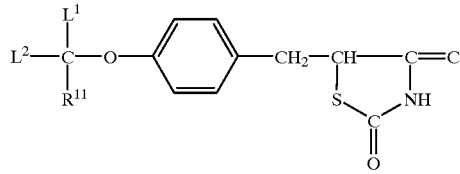

wherein $R^{11}$ is substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula

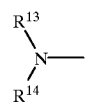

Possible Formrula Used for $R^{11}$ wherein $R^{13}$ and $R^{14}$ are the same or different and each is lower alkyl or $R^{13}$ and $R^{14}$ are combined to each other either directly or as interrupted by a heteroatom selected from the group consisting of nitrogen, oxygen, and sulfur to form a 5- or 6- membered ring;

wherein $R^{12}$ means a bond or lower alkylene group; and wherein $L^1$ and $L^2$ are the same or different and each is hydrogen or lower alkyl or $L^1$ and $L^2$ are combined to form an alkylene group; or a pharmaceutically acceptable salt thereof.

The present invention is also the use of compounds of the Formula III

Formula III

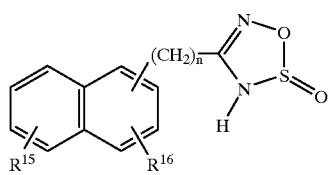

wherein $R^{15}$ and $R^{16}$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4 and the pharmaceutically acceptable salts thereof.

The present invention is also directed to the use of compounds of the Formula IV Formula IV

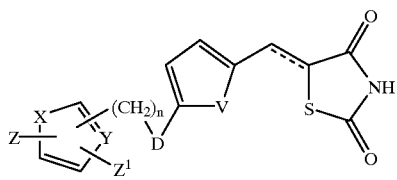

wherein the dotted line represents a bond or no bond;
V is —CH=CH—, —N=CH—, —CH=N— or S;
D is $CH_2$, CHOH, CO, C=$NOR_{17}$ or CH=CH;
X is S, O, $NR^{18}$, —CH=N or —N=CH;
Y is CH or N;
Z is hydrogen, $(C_1-C_7)$alkyl, $(C_1-C_7)$cycloalkyl, phenyl, naphthyl, pyridyl, furyl, thienyl, or phenyl mono- or disubstituted with the same or different groups which are $(C_1-C_3)$ alkyl, trifluoromethyl, $(C_1-C_3)$alkoxy, fluoro, chloro, or bromo;
$Z^1$ is hydrogen or $(C_1-C_3)$alkyl;
$R^{17}$ and $R^{18}$ are each independently hydrogen or methyl; and
n is 1, 2, or 3;
the pharmaceutically acceptable cationic salts thereof; and the pharmaceutically acceptable acid addition salts thereof when the compound contains a basic nitrogen.

The present invention is also directed to the use of compounds of the Formula V

Formula V

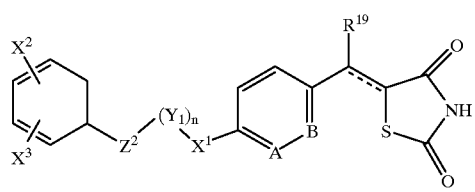

wherein the dotted line represents a bond or no bond;
A and B are each independently CH or N, with the proviso that when A or B is N, the other is CH;
$X^1$ is S, SO, $SO_2$, $CH_2$, CHOH, or CO;
n is 0 or 1;
$Y^1$ is $CHR^{20}$ or $R^{21}$, with the proviso that when n is 1 and $Y^1$ is $NR^{21}$, $X^1$ is $SO_2$ or CO;
$Z^2$ is $CHR^{22}$, $CH_2CH_2$, CH=CH,

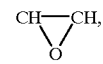

Possible Formula $Z^2$ $OCH_2$, $SCH_2$, $SOCH_2$ or $SO_2CH_2$;
$R^{19}$, $R^{20}$, $R^{21}$, and $R^{22}$ are each independently hydrogen or methyl; and
$X^2$ and $X^3$ are each independently hydrogen, methyl, trifluoromethyl, phenyl, benzyl, hydroxy, methoxy, phenoxy, benzyloxy, bromo, chloro, or fluoro;
a pharmaceutically acceptable cationic salt thereof; or
a pharmaceutically acceptable acid addition salt thereof when A or B is N.

The present invention also relates to the use of compounds of the Formula VI

Formula VI

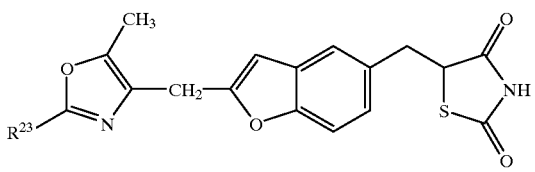

or a pharmaceutically acceptable salt thereof wherein $R^{23}$ is alkyl of 1 to 6 carbon atoms, cycloalkyl of 3 to 7 carbon atoms, phenyl or mono- or di-substituted phenyl wherein said substituents are independently alkyl of 1 to 6 carbon atoms, alkoxy of 1 to 3 carbon atoms, halogen, or trifluoromethyl.

The present invention also provides the use of a compound of Formula VII

Formula VII

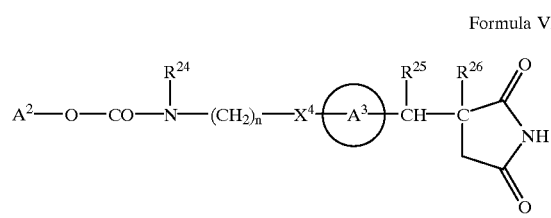

or a tautomeric form thereof and/or a pharmaceutically acceptable salt thereof, and/or a pharmaceutically acceptable solvate thereof, wherein:
$A^2$ represents an alkyl group, a substituted or unsubstituted aryl group, or an aralkyl group wherein the alkylene or the aryl moiety may be substituted or unsubstituted;
$A^3$ represents a benzene ring having in total up to 3 optional substituents;
$R^{24}$ represents a hydrogen atom, an alkyl group, an acyl group, an aralkyl group wherein the alkyl or the aryl moiety may be substituted or unsubstituted, or a substituted or unsubstituted aryl group; or $A^2$ together with $R^{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group;
$R^{25}$ and $R^{26}$ each represent hydrogen, or $R^{25}$ and $R^{26}$ together represent a bond;

$X^4$ represents O or S; and n represents an integer in the range from 2 to 6.

The present invention also provides the use of a compound of Formula VIII

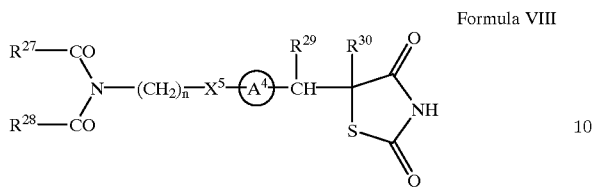

Formula VIII or a tautomeric form thereof and/or a pharmaceutically acceptable salt thereof, and/or a pharmaceutically acceptable solvate thereof, wherein:

$R^{27}$ and $R^{28}$ each independently represent an alkyl group, a substituted or unsubstituted aryl group, or an aralkyl group being substituted or unsubstituted in the aryl or alkyl moiety; or $R^{27}$ together with $R^{28}$ represents a linking group, the linking group consisting of an optionally substituted methylene group or an O or S atom, optional substituents for the said methylene groups being selected from alkyl-, aryl, or aralkyl, or substituents of adjacent methylene groups together with the carbon atoms to which they are attached form a substituted or unsubstituted phenylene group;

$R^{29}$ and $R^{30}$ each represent hydrogen, or $R^{29}$ and $R^{30}$ together represent a bond;

$A^4$ represents a benzene ring having in total up to 3 optional substituents;

$X^5$ represents O or S; and n represents an integer in the range from 2 to 6.

The present invention also provides the use of a compound of Formula IX

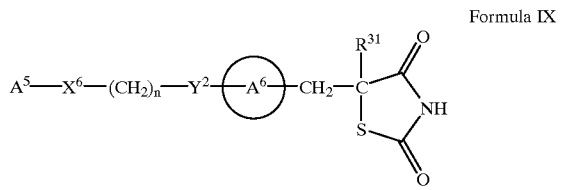

Formula IX or a tautomeric form thereof and/or a pharmaceutically acceptable salt thereof, and/or a pharmaceutically acceptable solvate thereof, wherein:

$A^5$ represents a substituted or unsubstituted aromatic heterocyclyl group;

$A^6$ represents a benzene ring having in total up to 5 substituents;

$X^6$ represents O, S, or $NR^{32}$ wherein $R^{32}$ represents a hydrogen atom, an alkyl group, an acyl group, an aralkyl group, wherein the aryl moiety may be substituted or unsubstituted, or a substituted or unsubstituted aryl group;

$Y^2$ represents O or S;

$R^{31}$ represents an alkyl, aralkyl, or aryl group; and n represents an integer in the range from 2 to 6.

Suitable aromatic heterocyclyl groups include substituted or unsubstituted, single or fused ring aromatic heterocyclyl groups comprising up to 4 hetero atoms in each ring selected from oxygen, sulfur, or nitrogen.

Favored aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2, or 3 heteroatoms, especially 1 or 2, selected from oxygen, sulfur, or nitrogen.

Suitable values for $A^5$ when it represents a 5-membered aromatic heterocyclyl group include thiazolyl and oxazoyl, especially oxazoyl.

Suitable values for $A^6$ when it represents a 6-membered aromatic heterocyclyl group include pyridyl or pyrimidinyl.

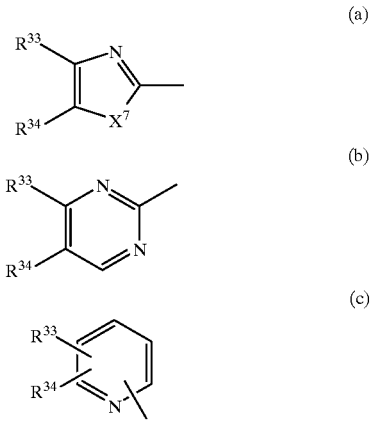

Suitable $R^{31}$ represents an alkyl group, in particular a $C_{1-6}$ alkyl group, for example a methyl group. Preferably, $A^5$ represents a moiety of formula (a), (b), or (c):

Formula (a), (b) and (c)

wherein:

$R^{33}$ and $R^{34}$ each independently represents a hydrogen atom, an alkyl group, or a substituted or unsubstituted aryl group or when $R^{33}$ and $R^{34}$ are each attached to adjacent carbon atoms, then $R^{33}$ and $R^{34}$ together with the carbon atoms to which they are attached form a benzene ring wherein each carbon atom represented by $R^{33}$ and $R^{34}$ together may be substituted or unsubstituted; and in the moiety of Formula (a), $X^7$ represents oxygen or sulfur.

In one favored aspect $R^{33}$ and $R^{34}$ together represent a moiety of Formula (d):

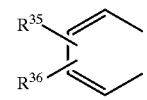

Formula (d)

wherein $R^{35}$ and $R^{36}$ each independently represent hydrogen, halogen, substituted or unsubstituted alkyl, or alkoxy.

The present invention also provides for the use of compounds for Formula X

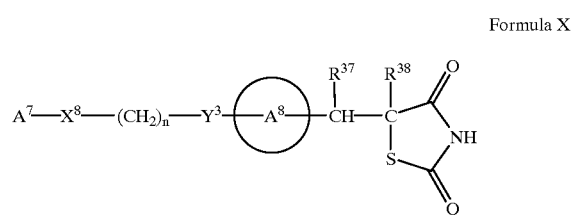

Formula X or a tautomeric form thereof and/or a pharmaceutically acceptable salt thereof, and/or a pharmaceutically acceptable solvate thereof, wherein:

$A^7$ represents a substituted or unsubstituted aryl group;

$A^8$ represents a benzene ring having in total up to 5 substituents;

$X^8$ represents O, S, or $NR^{39}$ wherein $R^{39}$ represents a hydrogen atom, an alkyl group, an acyl group, an aralkyl group, wherein the aryl moiety may be substituted or unsubstituted, or a substituted or unsubstituted aryl group;

$Y^3$ represents O or S;

$R^{37}$ represents hydrogen;

$R^{38}$ represents hydrogen or an alkyl, aralkyl, or aryl group or $R^{37}$ together with $R^{38}$ represents a bond; and n represents an integer in the range from 2 to 6.

The present invention is also directed to the use of compounds of Formula XI

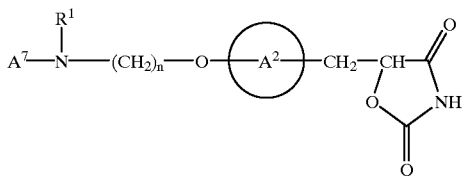

Formula XI or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to 5 substituents; and n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen. sulfur, or nitrogen.

Favored aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2, or 3 heteroatoms, especially 1 or 2, selected from oxygen, sulfur, or nitrogen.

Suitable values for $A^1$ when it represents a 5-membered aromatic heterocyclyl group include thiazolyl and oxazolyl, especially oxazoyl.

Suitable values for $A^1$ when it represents a 6-membered aromatic heterocyclyl group include pyridyl or pyrimidinyl.

Preferably, $A^5$ represents a moiety of formula (a), (b), or (c):

Formula (a), (b) and (c)

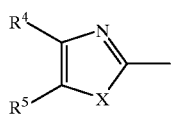

(a)

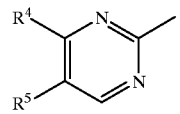

(b)

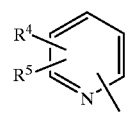

(c)

wherein:

$R^4$ and $R^5$ each independently represents a hydrogen atom, an alkyl group, or a substituted or unsubstituted aryl group or when $R^4$ and $R^5$ are each attached to adjacent carbon atoms, then $R^4$ and $R^5$ together with the carbon atoms to which they are attached form a benzene ring wherein each carbon atom represented by $R^4$ and $R^5$ together may be substituted or unsubstituted; and in the moiety of Formula (a), X represents oxygen or sulfur.

The present invention is also directed to the use of compounds of Formulas XII and XIII

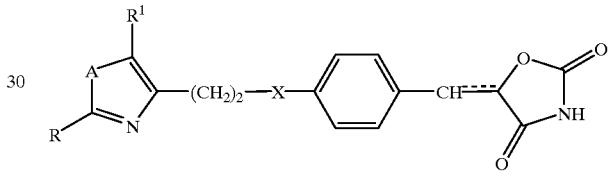

Formula XII

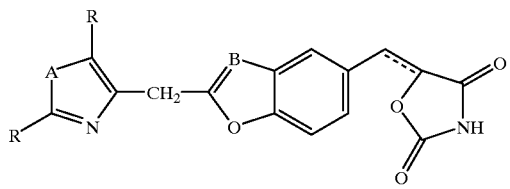

Formulas XIII or a pharmaceutically acceptable salt thereof wherein the dotted line represents a bond or no bond;

R is cycloalkyl of three to seven carbon atoms, naphthyl, thienyl, furyl, phenyl or substituted phenyl wherein said substituent is alkyl of one to three carbon atoms, alkoxy of one to three carbon atoms, trifluoromethyl, chloro, fluoro or bis(trifluoromethyl);

$R^1$ is alkyl of one to three carbon atoms;

X is O or C=O;

A is O or S; and

B is N or CH.

In one aspect the present invention is the use the compounds of Formulas I through Formula XIII, and Formulas Ia, Ib and Ic, for the treatment of the climacteric and of cancer. These compounds are herein referred to as thiazolidine derivatives. Where appropriate, the specific names of thiazolidine derivatives may be used including: Troglitazone, cioglitazone, pioglitazone and BRL 49653.

A preferred group of compounds are those of Formula XI wherein the dotted line represents no bond, $R^1$ is methyl, X is O and A is O. Especially preferred within this group are the compounds where R is phenyl, 2-naphthyl and 3,5-bis (trifluoromethyl)phenyl.

Another group of preferred compounds are those of Formula XII wherein the dotted line represents no bond, $R_1$ is methyl and A is O. Especially preferred within this group are compounds where B is CH and R is phenol, p-tolyl, m-tolyl, cyclohexyl, and 2-naphthyl. Also especially preferred is the compound where B is N and R is phenyl.

A still further embodiment of the present invention is the use of a pharmaceutical composition for administering an effective amount of a compound of the preceding Formulas I through XIII along with a pharmaceutically acceptable carrier in unit dosage form in the treatment methods mentioned above.

DETAILED DESCRIPTION OF THE PREFERRED EMBODIMENTS

Figure 1:
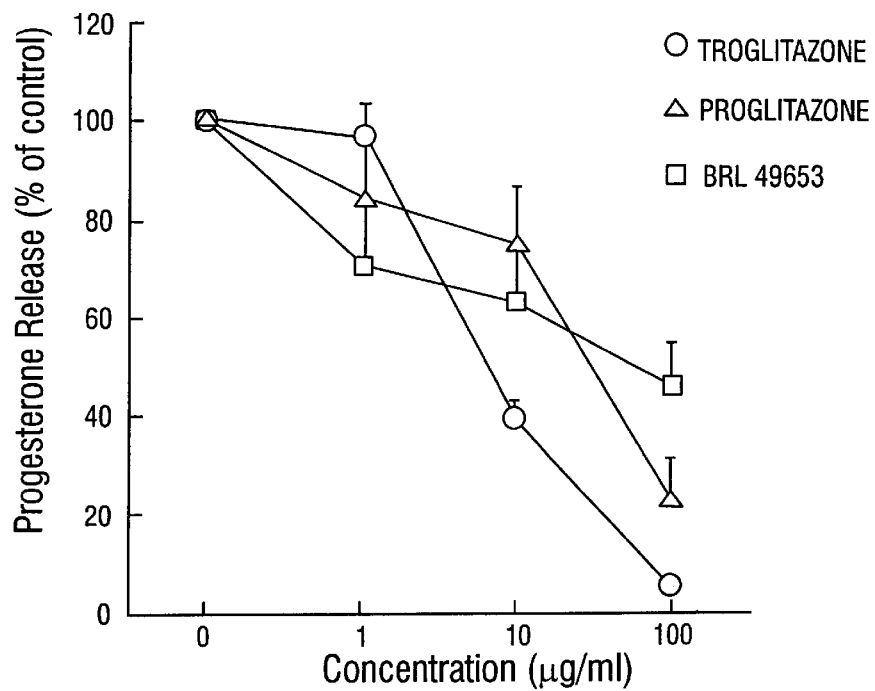
FIG. 1. Dose-response of progesterone production suppression in porcine granulosa cells treated with Troglitazone and related thiazolidinedione compounds. Porcine granulosa cells were treated for 24 h with increasing doses of Troglitazone, pioglitazone, and BRL 49653. The data represent the mean±SEM from 3 studies done in triplicate. Progesterone concentrations were corrected for DNA content in treated cells and are presented as a percentage of basal corrected progesterone production.

The compounds used in the treatment methods of the invention, which are 5-[4-(chromoanalkoxy)benzyl]-thiazolidene derivatives, may be represented by the Formulas (Ia), (Ib), and (Ic)

Formulas (Ia), (Ib), and (Ic)

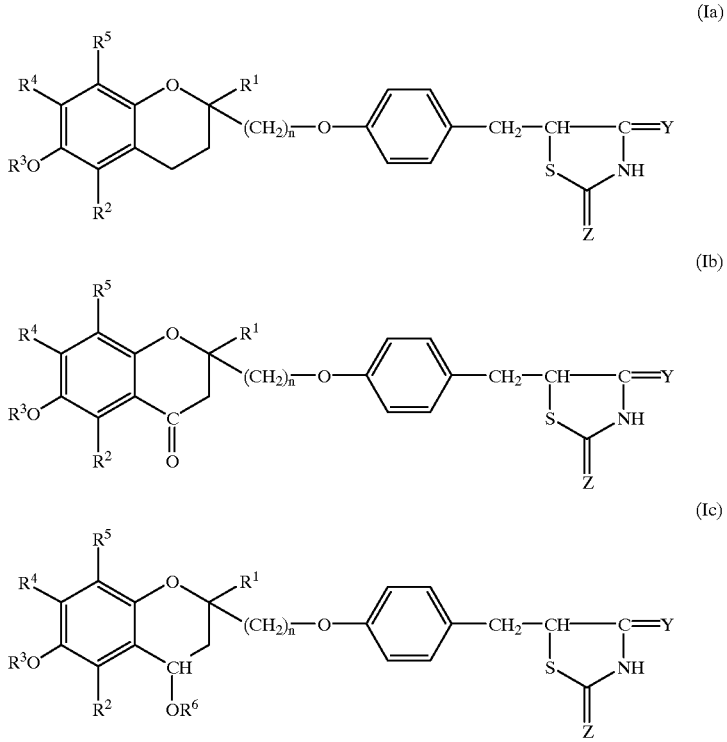

(in which $R^1$, $R^2$, $R^3$, $R^4$, $R^5$, $R^6$, n, Y, and Z are as defined above) and include pharmaceutically acceptable salts thereof.

In the compounds of the invention where $R^1$ or $R^2$ represents an alkyl group, this may be a straight or branched chain alkyl group having from 1 to 5 carbon atoms and is preferably a primary or secondary alkyl group, for example, the methyl, ethyl, propyl, isopropyl, butyl, isobutyl, pentyl, or isopentyl group.

Where $R^3$, $R^6$, or $R^{6'}$ represents al aliphatic acyl group, this preferably has from 1 to 6 carbon atoms and may include one or more carbon-carbon double or triple bonds. Examples of such groups include the fornyl, acetyl, propionyl, butyryl, isobutyryl, pivaloyl, hexanoyl, acryloyl, methacryloyl, and crotonyl groups.

Where $R^3$, $R^6$, or $R^{6'}$ represents an alicyclic acyl group, it is preferably a cyclopentanecarbonyl, cyclohexanecarbonyl, or cycloheptanecarbonyl group.

Where $R^3$, $R^6$, or $R^{6'}$ represents an aromatic acyl group, the aromatic moiety thereof may optionally have one or more substituents (for example, nitro, amino, alkylamino, dialkylamino, alkoxy, halo, alkyl, or hydroxy substituents); examples of such aromatic acyl groups included the benzoyl, p-nitrobenzoyl, m-fluorobenzoyl, o-chlorobenzoyl, p-aminobenzoyl, m-(dimethylamino)benzoyl, o-methoxybenzoyl, 3,4-dichlorobenzoyl, 3,5-di-t-butyl-4-hydroxy benzoyl, and 1-naphthoyl groups.

Where $R^3$, $R^6$, or $R^{6'}$ represents a heterocyclic acyl group, the heterocyclic moiety thereof preferably has one or more, preferably one, oxygen, sulfur, or nitrogen hetero atoms and has from 4 to 7 ring atoms; examples of such heterocyclic acyl groups include the 2-furoyl, 3-thenoyl, 3-pyridinecarbonyl (nicotinoyl), and 4-pyridinocarbonyl groups.

Where $R^3$, $R^6$, or $R^{6'}$ represents an aralphatic acyl group, the aliphatic moiety thereof may optionally have one or more carbon-carbon double or triple bonds and the aryl moiety thereof may optionally have one or more substituents (for example, nitro, amino, alkylamino, dialkylamino, alkoxy, halo, alkyl, or hydroxy substituents); examples of such aralphatic acyl groups include the phenylacetyl, p-chlorophenylacetyl, phenylpropionyl, and cinnamoyl groups.

Where $R^3$, $R^6$, or $R^{6'}$ represents a ($C_1$–$C_6$ alkoxy)carbonyl group, the alkyl moiety thereof may be any one of those alkyl groups as defined for $R^1$ and $R^2$, but is preferably a methyl or ethyl group, and the alkoxycarbonyl group represented by $R^3$, $R^6$, or $R^{6'}$ is therefore preferably a methoxycarbonyl or ethoxycarbonyl group.

Where $R^3$, $R^6$, or $R^{6'}$ represents an aralkyloxycarbonyl group, the aralkyl moiety thereof may be any one of those included within the aralphatic acyl group represented by $R^3$, $R^6$, or $R^{6'}$, but is preferably a benzyloxycarbonyl group.

Where $R^4$ and $R^5$ represent alkyl groups, they may be the same or different and may be straight or branched chain alkyl groups. They preferably have from 1 to 5 carbon atoms and examples include the methyl, ethyl, propyl, isopropyl, butyl, isobutyl, t-butyl, pentyl, and isopentyl groups.

Where $R^4$ and $R^5$ represent alkoxy groups, these may be the same or different and may be straight or branched chain groups, preferably having from 1 to 4 carbon atoms. Examples include the methoxy, ethoxy, propoxy, isopropoxy, and butoxy groups. Alternatively, $R^4$ and $R^5$ may together represent a $C_1$–$C_4$ alkylenedioxy group, more preferably a methylenedioxy or ethylenedioxy group.

Preferred classes of compounds of Formula I are as follows:

(1) Compounds in which $R^3$ represents a hydrogen atom, a $C_1$–$C_6$ aliphatic acyl group, an aromatic acyl group, or a heterocyclic acyl group.

(2) Compounds in which Y represents an oxygen atom; $R^1$ and $R^2$ are the same or different and each represents a hydrogen atom or a $C_1$–$C_5$ alkyl group; $R^3$ represents a hydrogen atom, a $C_1$–$C_6$ aliphatic acyl group, an aromatic acyl group, or a pyridinecarbonyl group; and $R^4$ and $R^5$ are the same or different and each represents a hydrogen atom, a $C_1$–$C_5$ alkyl group, or a $C_1$ or $C_2$ alkoxy group.

(3) Compounds as defined in (2) above, in which $R^1$, $R^2$, $R^4$ and $R^{5'}$ are the same or different and each represents a hydrogen atom or a $C_1$–$C_5$ alkyl group; n is 1 or 2; and W represents the —$CH_2$— or >CO group.

(4) Compounds as defined in (3) above, in which $R^3$ represents a hydrogen atom, a $C_1$–$C_5$ aliphatic acyl group, a benzoyl group, or a nicotinyl group.

(5) Compounds as defined in (4) above, in which: $R^1$ and $R^4$ are the same or different and each represents a $C_1$–$C_5$ alkyl group; $R^2$ and $R^5$ are the same or different and each represents the hydrogen atom or the methyl group; and $R^3$ represents a hydrogen atom or a $C_1$–$C_4$ aliphatic acyl group.

(6) Compounds in which: W represents the —$CH_2$— or >CO group; Y and Z both represent oxygen atoms; n is 1 or 2; $R^1$ and $R^4$ are the same or different and each represents a $C_1$–$C_4$ alkyl group; $R^2$ and $R^5$ are the same or different and each represents the hydrogen atom or the methyl group; and $R^3$ represents a hydrogen atom or a $C_1$–$C_4$ aliphatic acyl group.

(7) Compounds as defined in (6) above, in which n is 1.

(8) Compounds as defined in (6) or (7) above, in which W represents the —$CH_2$— group.

Preferred compounds among the compounds of Formula I are those wherein:
$R^1$ is a C1–C4 alkyl group, more preferably a methyl or isobutyl group, most preferably a methyl group;
$R^2$ is a hydrogen atom or a $C_1$–$C_4$ alkyl group, preferably a hydrogen atom, or a methyl or isopropyl group, more preferably a hydrogen atom or a methyl group, most preferably a methyl group;
$R^3$ is a hydrogen atom, a $C_1$–$C_4$ aliphatic acyl group, an aromatic acyl group or a pyridinecarbonyl group, preferably a hydrogen atom, or an acetyl, butyryl, benzoyl, or nicotinyl group, more preferably a hydrogen atom or an acetyl, butyryl or benzoyl group, most preferably a hydrogen atom or an acetyl group;
$R^4$ is a hydrogen atom, a $C_1$–$C_4$ alkyl group or a $C_1$ or $C_2$ alkoxy group, preferably a methyl, isopropyl, t-butyl, or methoxy group, more preferably a methyl or t-butyl group, most preferably a methyl group;
$R^5$ is a hydrogen atom, a $C_1$–$C_4$ alkyl group or a $C_1$ or $C_2$ alkoxy group, preferably a hydrogen atom, or a methyl or methoxy group, more preferably a hydrogen atom or a methyl group, and most preferably a methyl group;
n is 1 or 2, preferably 1;
Y is an oxygen atom;
Z is an oxygen atom or an imino group, most preferably an oxygen atom; and
W is a —$CH_2$— or >C=O group, preferably a —$CH_2$ group.

Referring to the general Formula II, the substituents may be any from 1 to 3 selected from nitro, amino, alkylamino, dialkylamino, alkoxy, halo, alkyl, or hydroxy, the aromatic acyl group may be benzoyl and naphthoyl. The alkyl group $R^{11}$ may be a straight chain or branched alkyl of 1 to 10 carbon atoms, such as methyl, ethyl, n-propyl, i-propyl, n-butyl, i-butyl, t-butyl, n-pentyl, i-pentyl, n-hexyl, n-heptyl, n-octyl, n-nonyl, and n-decyl; the cycloalkyl group $R^{11}$ may be a cycloalkyl group of 3 to 7 carbon atoms, such as cyclopropyl, cyclopentyl, cyclohexyl, and cycloheptyl and the phenylalkyl group $R^{11}$ may be a phenylakyl group of 7 to 11 carbon atoms such as benzyl and phenethyl. As examples of the heterocyclic group $R^{11}$ may be mentioned 5- or 6-membered groups each including 1 or 2 hetero-atoms selected from among nitrogen, oxygen, and sulfur, such as pyridyl, thienyl, furyl, thiazolyl, etc. When $R^{11}$ is

Possible Formula Used for $R^{11}$ the lower alkyls $R^{13}$ and $R^{14}$ may each be a lower alkyl of 1 to 4 carbon atoms, such as methyl, ethyl, n-propyl, i-propyl, and n-butyl. When $R^{13}$ and $R^{14}$ are combined to each other to form a 5- or 6-membered heterocyclic group as taken together with the adjacent N atom, i.e., in the form of

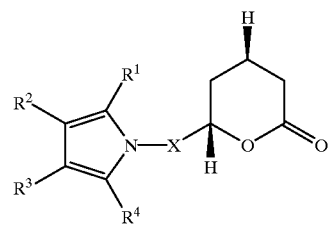

$R^{13}$ and $R^{14}$ are combined to each other to form a 5- or 6-membered heterocyclic group this heterocyclic group may further include a heteroatom selected from among nitrogen, oxygen, and sulfur as exemplified by piperidino, morpholino, pyrrolidino, and piperazino. The lower alkylene group $R^{12}$ may contain 1 to 3 carbon atoms and thus may be, for example, methylene, ethylene, or trimethylene. The bond $R^{12}$ is equivalent to the symbol "-", ".", or the like which is used in chemical structural formulas, and when $R^{12}$ represents such a bond, the compound of general Formula II is represented by the following general Formula II(a)

Formula II(a)

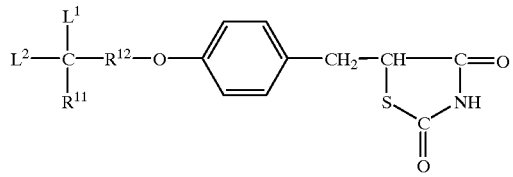

Thus, when $R^{12}$ is a bond, the atoms adjacent thereto on both sides are directly combined together. As examples of the lower alkyls $L^1$ and $L^2$, there may be mentioned lower alkyl groups of 1 to 3 carbon atoms, such as methyl and ethyl. The alkylene group formed as $L^1$ and $L^2$ are joined together is a group of the formula —$(CH_2)_n$-[where n is an integer of 2 to 6]. The cycloalkyl, phenylalkyl, phenyl, and heterocyclic groups mentioned above, as well as said heterocyclic group

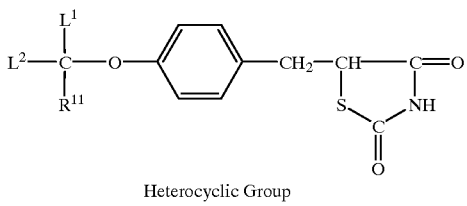

Heterocyclic Group may have 1 to 3 substituents in optional positions on the respective rings. As examples of such substituents may be mentioned lower alkyls (e.g., methyl, ethyl, etc.), lower alkoxy groups (e.g., methoxy, ethoxy, etc.), halogens (e.g., chlorine, bromine, etc.), and hydroxyl. The case also falls within the scope of the general Formula II that an alkylenedioxy group of the formula —O—$(CH_2)_m$—O— [is an integer of 1 to 3], such as methylenedioxy, is attached to the two adjacent carbon atoms on the ring to form an additional ring.

The preferred compounds of Formula III are those wherein $R^{15}$ and $R^{16}$ are independently hydrogen, lower alkyl containing 1 to 6 carbon atoms, alkoxy containing 1 to 6 carbon atoms, halogen, ethynyl, nitrile, trifluoromethyl, vinyl, or nitro; n is 1 or 2 and the pharmaceutically acceptable salts thereof.

Preferred in Formula IV are compounds wherein the dotted line represents no bond, particularly wherein D is CO or CHOH. More preferred are compounds wherein V is —CH=CH—, —CH=N— or S and n is 2, particularly those compounds wherein X is O and Y is N, X is S and Y is N, X is S and Y is CH or X is —CH=N— and Y is CH. In the most preferred compounds X is O or S and Y is N forming an oxazol-4-yl, oxazol-5-yl, thiazol-4-yl, or thiazol-5-yl group; most particularly a 2-[(2-thienyl), (2-furyl), phenyl, or substituted phenyl]-5-methyl-4-oxazolyl group.

The preferred compounds in Formula V are:

a) those wherein the dotted line represents no bond. A and B are each CH, $X^1$, is CO, n is O, $R^{19}$ is hydrogen, $Z^2$ is $CH_2CH_2$ or CH=CH and $X^3$ is hydrogen, particularly when $X^2$ is hydrogen, 2-methoxy, 4-benzyloxy, or 4-phenyl;

b) those wherein A and B are each CH, $X^1$ is S or $SO_2$, n is O, $R^{19}$ is hydrogen, $Z^2$ is $CH_2CH_2$ and $X^3$ is hydrogen, particularly when $X^2$ is hydrogen or 4-chloro.

c)

A preferred group of compounds is that of Formula VI wherein $R^{23}$ is $(C_1-C_6)$alkyl, $(C_3-C_7)$cycloalkyl, phenyl, halophenyl, or $(C_1-C_6-)$alkylphenyl. Especially preferred within this group are the compounds where $R^{23}$ is phenyl, methylphenyl, fluorophenyl, chlorophenyl, or cyclohexyl.

When used herein with regard to Formulas VII through X, the term "aryl" includes phenyl and naphthyl, suitably phenyl, optionally substituted with up to 5, preferably up to 3, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

The term "halogen" refers to fluorine, chlorine, bromine, and iodine; preferably chlorine.

The terms "alkyl" and "alkoxy" relate to groups having straight or branched carbon chains, containing up to 12 carbon atoms.

Suitable alkyl groups are $C_{1-12}$ alkyl groups, especially $C_{1-6}$ alkyl groups, e.g., methyl, ethyl, n-propyl, iso-propyl, n-butyl, isobutyl, or tert-butyl groups.

Suitable substituents for any alkyl group include those indicated above in relation to the term "aryl".

Suitable substituents for any heterocyclyl group include up to 4 substituents selected from the group consisting of alkyl, alkoxy, aryl, and halogen or any 2 substituents on adjacent carbon atoms, together with the carbon atoms to which they are attached, may form an aryl group, preferably a benzene ring, and wherein the carbon atoms of the aryl group represented by the said 2 substituents may themselves be substituted or unsubstituted.

Specific examples of compounds of the present invention are given in the following list:

(+)-5-[[4-[(3,4-dihydro-6-hydroxy-2,5,7,8-tetramethyl-2H-1-benzopyran-2-yl)methoxy] phenyl]methyl]-2,4-thiazolidinedione: (Troglitazone);

5-[4-[2-(5-ethylpyridin-2-yl)ethoxyl]benzyl] thiadiazolidine-2,4-dione: (pioglitazone);

5-[4-[(1-methylcyclohexyl)methoxy]benzyl] thiadiazolidine-2,4-dione: (ciglitazone);

4-(2-naphthylmethyl)-1,2,3,5-oxathiadiazole-2-oxide;

5-[4-[2-[N-(benzoxazol-2-yl)-N-methylamino]ethoxy] benzyl]-5-methylthiazolidine-2,4-dione;

5-[4-[2-[2,4-dioxo-5-phenylthiazolidin-3-yl)ethoxy]benzyl] thiazolidine-2,4-dione;

5-[4-[2-[N-methyl-N-(phenoxycarbonyl)amino]ethoxy] benzyl]thiazolidine-2,4-dione;

5-[4-[2-phenoxyethoxy)benzyl]thiazolidine-2,4-dione;

5-[4-[2-(4-chlorophenyl)ethylsulfonyl]benzyl]thiazolidine-2,4-dione;

5-[4-[3-(5-methyl-2-phenyloxazol-4-yl)propionyl]benzyl] thiazolidine-2,4-dione;

5-[[4-(3-hydroxy-1-methylcyclohexyl)methoxy]benzyl] thiadiazolidine-2,4-dione;

5-[4-[2-(5-methyl-2-phenyloxazol-4-yl)ethoxyl]benzyl] thiadizolidione-2,4-dione;

5-[(2-benzyl-2,3-dihydrobenzopyran)-5-ylmethyl] thiadiazoline-2,4-dione: (englitazone);

5-[[2-(2-naphthylmethyl)benzoxazol]-5-ylmethyl] thiadiazoline-2,4-dione;

5-[4-[2-(3-phenylureido)ethoxyl]benzyl]thiadiazoline-2,4-dione;

5-[4-[2-[N-(benzoxazol-2-yl)-N-methylamino]ethoxy] benzyl]thiadiazoline-2,4-dione;

5-[4-[3-(5-methyl-2-phenyloxazol-4-yl)propionyl]benzyl] thiadiazoline-2,4-dione;

5-[2-(5-methyl-2-phenyloxazol-4-ylmethyl)benzofuran-5-ylmethyl]-oxazolidine-2,4-dione;

5-[4-[2-[N-methyl-N-(2-pyridyl)amino]ethoxy]benzyl] thiazolidine-2,4-dione (BRL 49653); and 5-[4-[2-[N-(benzoxazol-2-yl)-N-methylamino]ethoxy] benzyl]-oxazolidine-2,4-dione.

The compounds of Formulas I through XIII are capable of further forming pharmaceutically acceptable acid addition and/or base salts.

The compounds of Formulas I through XIII are capable of further forming both pharmaceutically acceptable acid addition and/or base salts. All of these forms are within the scope of the present invention.

Pharmaceutically acceptable acid addition salts of the compounds of Formulas I through XIII include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoracetate, propionate, caprylate, isobutyrate, oxalate, malonate, succinate, suberate, sebacate, fumarate, malcate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge et al., 1977).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are $N_2N'$-dibenzylethylenediamine, chloroprocaine, choline, diethanolamine, dicyclohexylamine, ethylenediamine, N-methylglucamine, and procaine (see, for example, Berge et al., 1977).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention. Certain of the compounds of the present invention possess one or more chiral centers and each center may exist in different configurations. The compounds can, therefore, form stereoisomers. Although these are all represented herein by a limited number of molecular formulas, the present invention includes the use of both the individual, isolated isomers and mixtures, including racemates, thereof. Where stereospecific synthesis techniques are employed or optically active compounds are employed as starting materials in the preparation of the compounds, individual isomers may be prepared directly; on the other hand, if a mixture of isomers is prepared, the individual isomers may be obtained by conventional resolution techniques, or the mixture may be used as is, without resolution.

Furthermore, the thiazolidene or oxazlidene part of the compounds of Formulas I through XIII can exist in the form of tautomeric isomers. All of the tautomers are represented by Formulas I through XIII, and are intended to be a part of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the size and shape desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active compound is dispersed homogeneously therein, as by stirring. The molten homogenous mixture is then poured into convenient sized molds, allowed to cool, and thereby to solidify.

Liquid form preparations include solutions, suspensions, and emulsions, for example, water or water proylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

The compounds of Formulas I through XIII are valuable agents for the treatment of the climacteric and of cancer. The following illustrates testing to show that compounds have the disclosed activity, using the preferred compound Troglitazone and related thiazolidinedione derivatives.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Suppression of Progesterone Production in Porcine Granulosa Cells with Troglitazone and Related Compounds Initial studies investigated the dose-response of Troglitazone and related compounds on progesterone production in cultures of porcine granulosa cells. Porcine granulosa cells were isolated from 1- to 5-mm follicles of ovaries from immature swine (60–70 kg) obtained from a local slaughterhouse (Urban el al., 1994). The cells were plated in Eagle's minimum essential medium and 3% fetal calf serum (FCS) at a concentration of 20–30 million cells/60-mm dish for 12–16 h to facilitate granulosa cell attachment to the plates. Monolayer cultures were maintained at 37° C. in 5% $CO_2$ throughout the study. After granulosa cell attachment, medium containing the FCS was discarded and serum-free medium with varying concentrations of Troglitazone, pioglitazone and BRL 49653 was added for 24 h. One ml of medium was collected for measurement of progesterone by an assay previously described that uses the chromatographic separation of steroids to enhance specificity (Urban et al., 1994). As shown in FIG. 1, all three of the drugs suppressed progesterone production by porcine granulosa cells in a dose-dependent fashion, but Troglitazone was more potent at suppressing progesterone production than 2 other drugs in the thiazolidinedione class of drugs (FIG. 1). This demonstrated the likely utility of Troglitazone and related thiazolidinedione derivatives in the treatment of the climacteric, and that thiazolidine derivatives have physiologic activities similar to those of Troglitazone.

Figure 2:
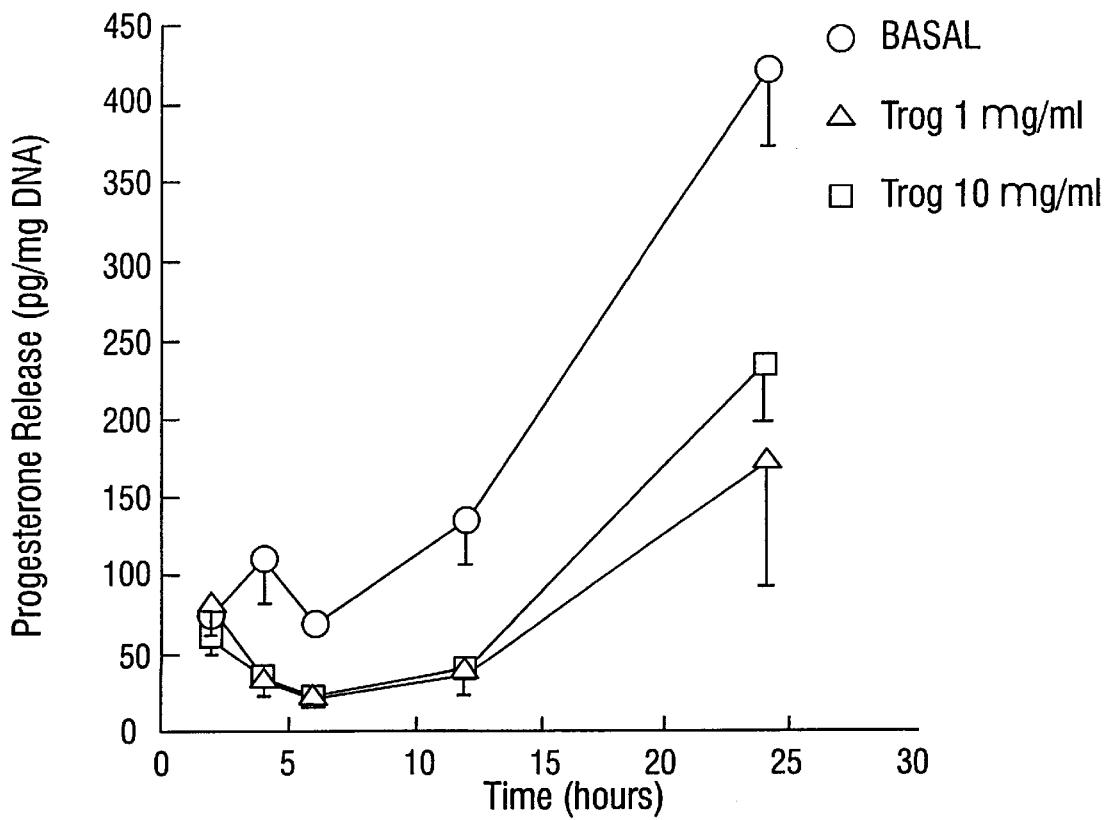
FIG. 2. Time course of Troglitazone suppression of progesterone production by porcine granulosa cells. Cultures of porcine granulosa cells were treated with Troglitazone, 1 and 10 µg/ml at 2,4,6,12, and 24 h. Progesterone production (corrected for DNA content) was measured as shown above. The data represent the mean±SEM from 3 studies done in triplicate.

The time course for the suppression of progesterone was done in the same porcine granulosa cell culture system. Cells were treated for up to 24 h with zero, 1, or 10 $\mu$g/ml of Troglitazone. As shown in FIG. 2, progesterone production was suppressed by Troglitazone as early as 4 h. The concentration of Troglitazone did not affect the time of onset of suppression (FIG. 2).

EXAMPLE 2

Cell Viability of Porcine Granulosa Cells During Treatment With Troglitazone

Figure 3:
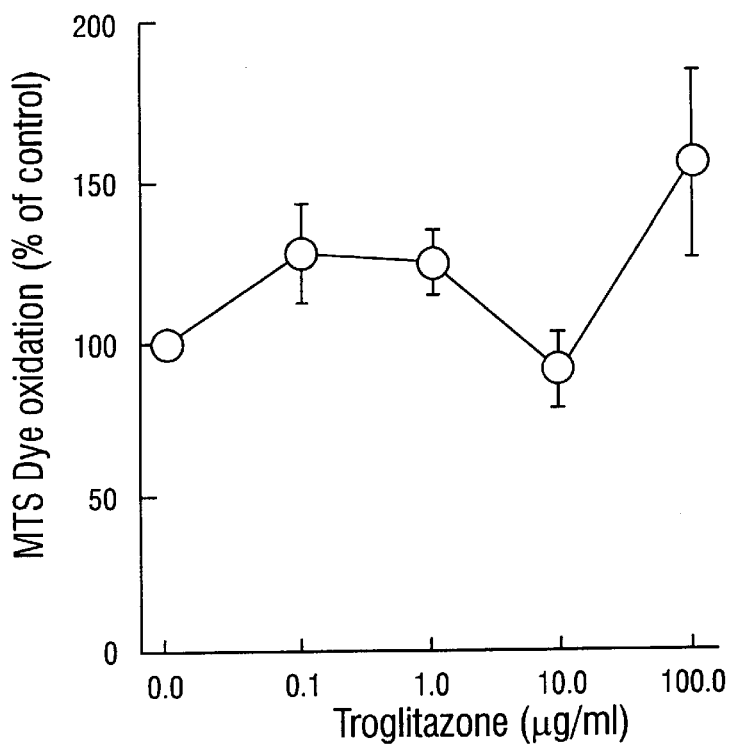
FIG. 3. Cell viability of porcine granulosa cells during treatment with Troglitazone. Porcine granulosa cells were treated with various concentrations of Troglitazone and cell viability determined using a MTS dye oxidation method. This method is based on the ability of dehydrogenase enzymes found in metabolically active cells to oxidize MTS to formazan. This compound is soluble in tissue culture medium. Data represent the mean±SEM from 2 studies done in triplicate.

Although there was not a significant decrease in DNA content between control and Troglitazone-treated porcine granulosa cells, total protein concentrations were lower in the Troglitazone treatment groups. Therefore, cell viability was tested in these cells using a calorimetric assay that is dependent on the oxidation of MTS to formazan (absorbance measured at 490 nm) by dehydrogenase enzymes found in metabolically active cells (Promega, Madison Wis.). This assay was verified in porcine granulosa cells by showing a linear increase in absorption with increasing cell density. Even at the highest doses of Troglitazone (100 $\mu$g/ml), there was not a decrease in cell viability in granulosa cells (FIG. 3). This demonstrates that Troglitazone and related thiazolidinedione derivatives are unlikely to affect the viability of normal granulosa cells.

EXAMPLE 3

Figure 4:
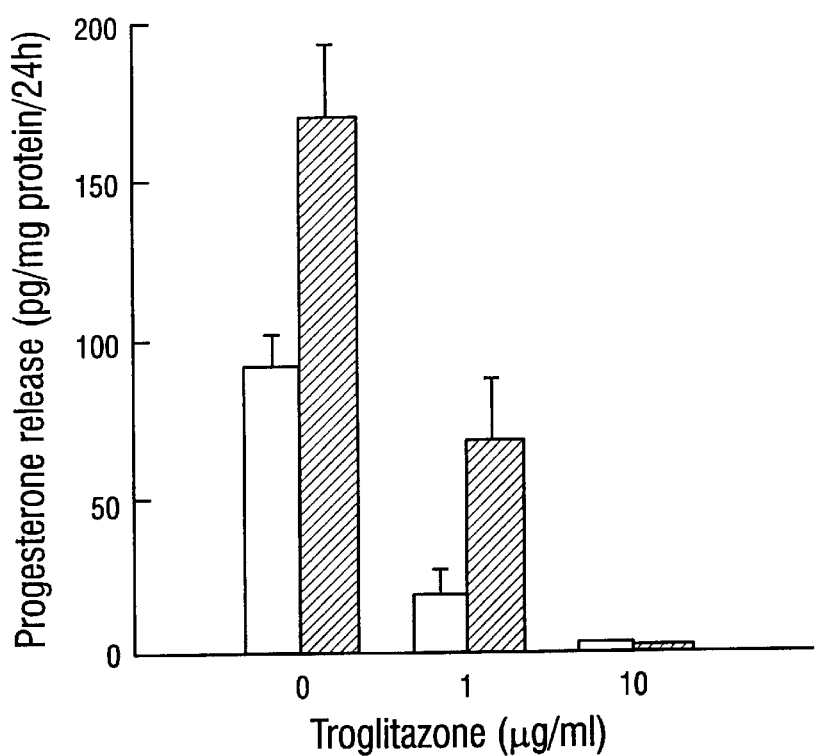
FIG. 4. Effects of 25-OH cholesterol on Troglitazone suppression of porcine granulosa cell progesterone production. Porcine granulosa cells were cultured for 24 h in serum-free medium (clear bars) or in the presence of 30 µg/ml of 25-OH cholesterol (shaded bars). Under both conditions, cells were treated with Troglitazone at a 1 and 10 µg/ml concentration. Data represent mean±SEM from 2 studies done in triplicate.

Studies on the Mechanism of Troglitazone Suppression of Porcine Granulosa Cell Progesterone Production The suppression of progesterone production in porcine granulosa cells by Troglitazone could be due to effects of the drug on the supply of cholesterol to the mitochondria. Before investigating proteins in the pathway of cholesterol transport to the mitochondria, it was first tested whether Troglitazone would inhibit progesterone production when cells were co-treated with 25-OH cholesterol. This compound diffuses directly to the P-450 cholesterol side-chain cleavage enzyme (P450scc) in the mitochondria and acts as a substrate for progesterone production (Veldhuis and Furlanetto, 1985). Treatment of porcine granulosa cells with Troglitazone and 25-OH cholesterol demonstrated that even in the presence of 25-OH cholesterol, Troglitazone suppressed progesterone production (FIG. 4).

Figure 5:
FIG. 5. Northern blot of Troglitazone effects on mRNA concentrations of P450scc. Northern blot hybridization with porcine P450scc cDNA clone of RNA (20 µg) obtained from porcine granulosa cells treated for 24 h with Troglitazone (5 µg/ml). L represents the ladder; B represents control granulosa total RNA, and T represents cell treated with Troglitazone 5 µg/ml for 24 h. Collection of total RNA and methods for Northern blot hybridization have been previously described (Urban et al., 1990).

Having shown that Troglitazone did not impair the cholesterol transport system in porcine granulosa cells, the effects of the drug on the mRNA concentrations of the rate-limiting enzyme in the steroidogenic pathway, P450scc, were determined (Miller, 1988). Suppression of transcription of this enzyme would result in decreased progesterone production by granulosa cells. Porcine granulosa cells were cultured and treated with Troglitazone (5 $\mu$g/ml) for 24 h. Troglitazone treatment did not suppress mRNA concentrations of P450scc (FIG. 5) suggesting that the compound does not inhibit progesterone synthesis by decreasing expression of this specific enzyme.

Figure 6:
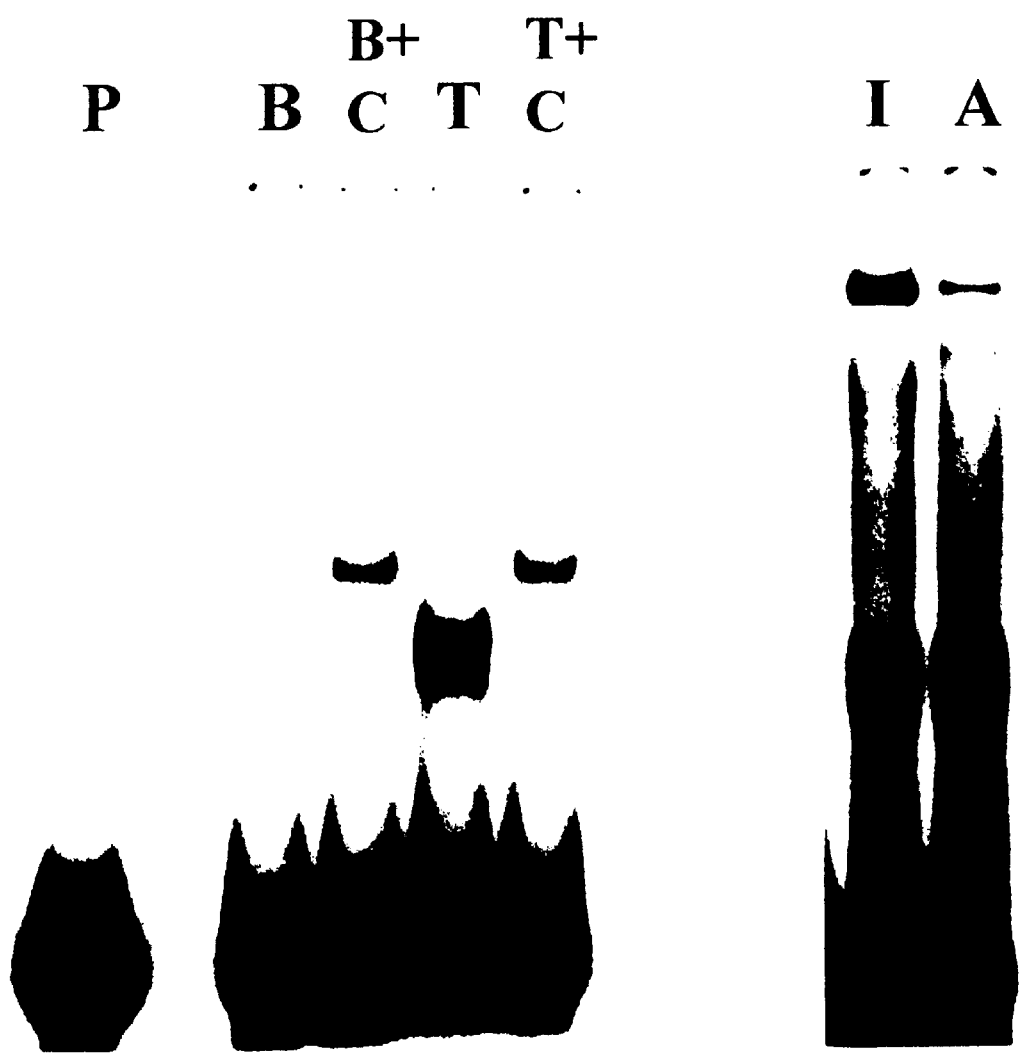
FIG. 6. An electrophoretic mobility gel shift assay (EMSA) of nuclear extract protein from porcine granulosa treated with Troglitazone. Porcine granulosa cells were treated with Troglitazone 5 µg/ml for 24 h and nuclear extract proteins collected. Extract (15 µg) was mixed with a $P^{32}$-labeled consensus PPRE oligonucleotide and run on a 4% polyacrylamide gel. P is the probe alone, B is control extract, B+C is control plus 100X unlabeled PPRE, T is Troglitazone treatment (5 µg/ml), and T+C is Troglitazone plus 100X unlabeled PPRE. I is the addition of rabbit serum and A is the addition of a PPARγ antibody. The arrow indicates the supershifted PPARγ band.

With no evidence of a direct effect of Troglitazone on the transport of cholesterol or the mRNA concentrations of the rate-limiting enzyme for steroidogenesis, P450scc, a more general effect of Troglitazone on cellular function was studied. As stated above, Troglitazone is a ligand for the PPARγ orphan nuclear receptor (Lehmann, 1995). This receptor binds to a DR-1 consensus element that is non-specific and will bind many transcription factors in this nuclear receptor family. It was indicated that a marked translocation of PPARγ into the nucleus could disrupt the function of many genes. This mechanism would make rapidly growing cells expressing PPARγ, such as those of many types mesenchymal tumors, more susceptible to this phenomenon. A DR-1 consensus oligonucleotide was synthesized (NNN-AGGTCA-N-AGGTCA, SEQ ID NO: 1) and used in electrophoretic mobility gel shift assay (EMSA) with 15 $\mu$g of nuclear extract protein from porcine granulosa cells treated with Troglitazone, pioglitazone and BRL 49653. All three of the compounds, Troglitazone, pioglitazone and BRL 49653 increased binding to the PPRE in granulosa cell nuclear extracts (FIG. 6), indicating that all three compounds had a similar effect with respect to binding of the DR-1 consensus sequence, although the binding was greatest with Troglitazone. Binding was specific in that unlabeled PPRE competitively inhibited binding of the labeled DNA (FIG. 6). Moreover, an antibody to PPARγ showed a supershifted band in EMSA (FIG. 6).

To further correlate the enhanced binding of PPARγ to the DR-1 consensus sequence after treatment with Troglitazone, cultures of porcine granulosa cells were treated with

EXAMPLE 7

Treatment of the Climacteric with Troglitazone

A female human patient typically enters the climacteric from about age 40 to age 55, resulting in irregular menses and episodes of prolonged bleeding. In the case of a patient with a history of deep venous thrombosis, severe hypertension, severe hyperlipidemia, breast cancer, endometrial cancer, or cholelithiasis, Troglitazone would be the primary treatment option. In the absence of these risk factors, Troglitazone may be offered as an option to hormone treatment. Prevention of irregular menstrual bleeding may be achieved in a human climacteric patient by administration of a therapeutically active amount of Troglitazone. During an initial treatment period, administration of Troglitazone in an amount of about 200 mg per day may be directed with monitoring of condition. If symptoms continue, administration may be increased to about 400 mg per day. Estrogen levels in the patient can be periodically monitored for low estrogen levels or symptoms of low estrogen levels, such as hot flashes. Treatment with Troglitazone may continue until these symptoms develop or there is evidence that the patient is menopausal. Such evidence may be suggested by an elevation in levels of follicle stimulating hormone.

EXAMPLE 8

Treatment of a Human Cancer Patient with Troglitazone

Figure 7A:
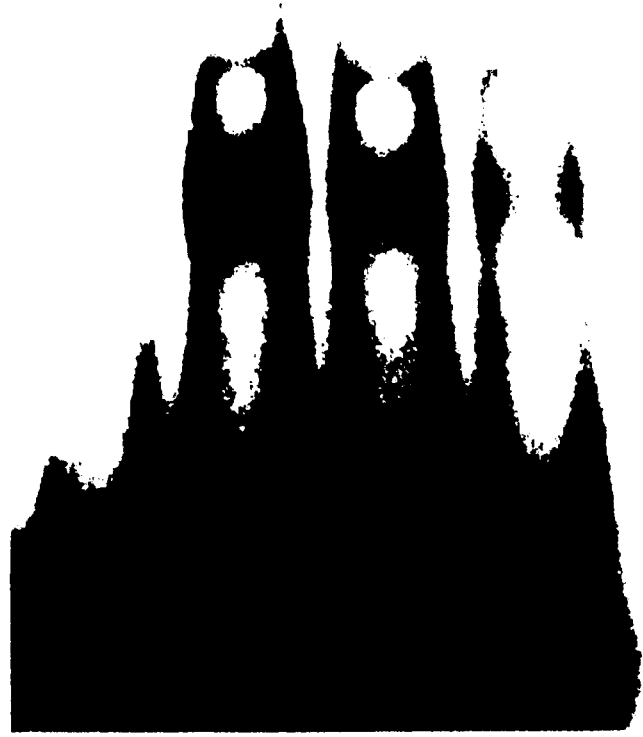
FIG. 7. Correlation of Troglitazone suppression of progesterone production with binding of PPARγ to a consensus PPRE. Panel A is an autoradiogram of a EMSA from nuclear extract protein from porcine granulosa cells treated for 24 h as such: B, control cells; T, Troglitazone 5 µg/ml; BR, BRL 49635 5 µg/ml; and P, pioglitazone 5 µg/ml. The nuclear extract was mixed with radioactively-labeled consensus PPRE as described in FIG. 6. Panel B is a graph of the progesterone values from the same porcine granulosa cells treated as described in A.
Figure 7B:
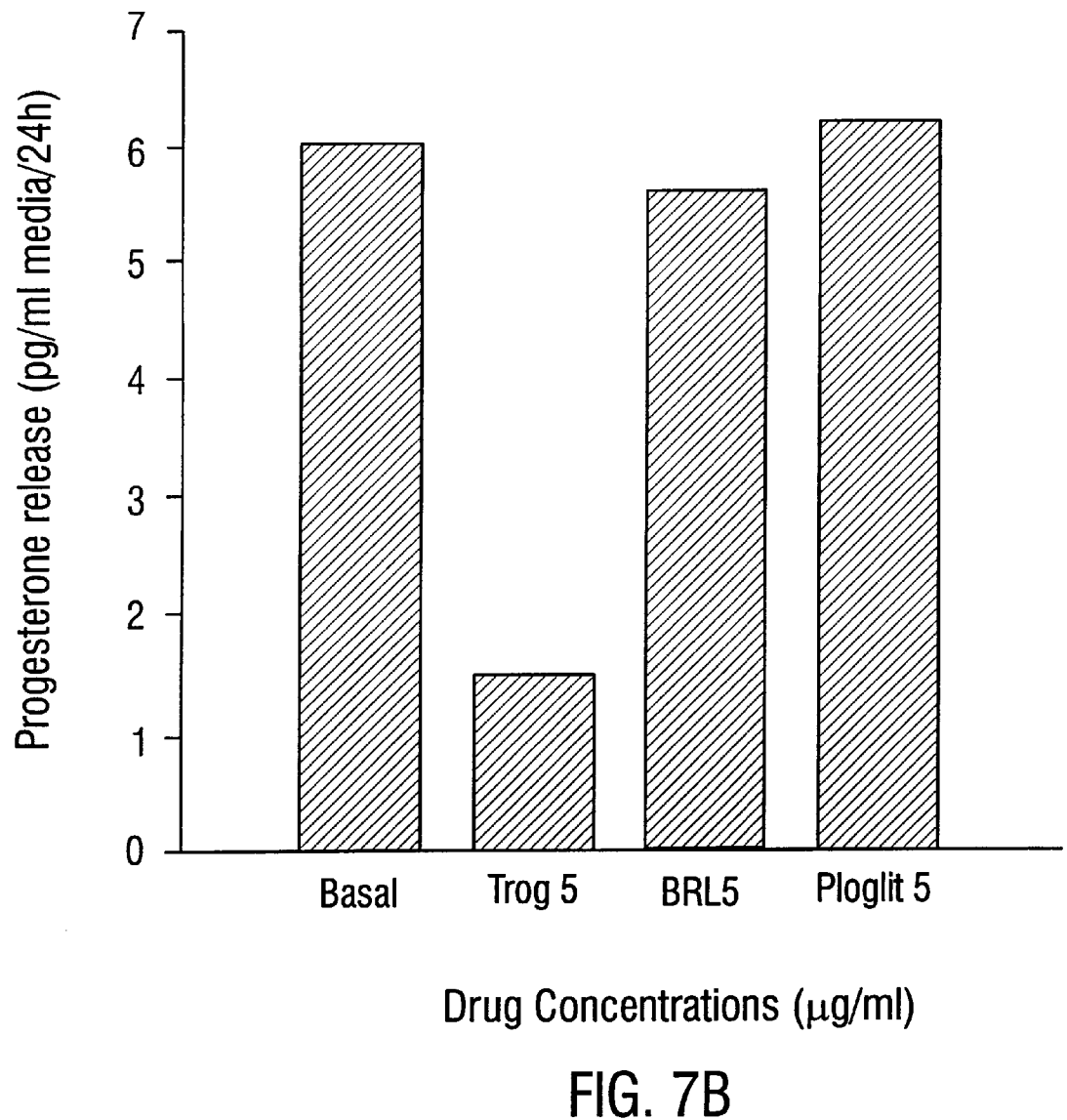

Troglitazone may be used for the treatment of tumor cells expressing PPARγ. The studies documented herein, demonstrate that Troglitazone can be used to reduce the viability of PPARγ-expressing cell lines, and that rapidly growing cells are particularly sensitive to Troglitazone. Thus tumors that are known to express PPARγ would be tumor types likely to be treated with troglitazone. Mesenchymal tumors are one type of tumor which is particularly likely to express PPARγ. In cases where it is not known if a tumor expresses PPARγ, one may use a number of methods to screen tumor cells for expression of PPARγ including EMSA, as well as Northern and Western Blot analysis. Tumor cell lines may be also be screened for sensitivity to Troglitazone in vitro or in vivo. Cultured tumor cells may be treated with concentrations of Troglitazone varying from about 0.1 μg to about 30 μg. Viability of the tumors cells may then be assayed using a colorimetric assay that is dependent on the oxidation of MTS to formazan (absorbance measured at 490 nm) by dehydrogenase enzymes found in metabolically active cells (Promega, Madison Wis.). In vivo treatment of a human cancer patient with Troglitazone may be achieved by administration of about 400 mg per day of Troglitazone. An initial period of treatment with Troglitazone or a thiazolidinedione derivative of a cancer patient may be initiated with monitoring of condition. Treatment may be continued or discontinued based on condition of the patient. Use of Troglitazone therapy in conjunction with other chemotherapeutic agents, radiation, or surgery may in many cases be the preferred mode of treatment. Troglitazone treatment therefore, would inhibit the growth of the cancer so that other therapies may be added, thereby increasing the likelihood of curing the patient. Troglitazone and related thiazolidinedione derivatives may additionally be used to treat patients with severely metastatic disease. Such treatment may slow tumor growth and reduce tumor mass, thereby prolonging survival and increasing the quality of life of terminal cancer patients. Troglitazone, pioglitazone, and BRL 49653 (all at a 5 μg/ml concentration) and nuclear extract protein was collected. As shown in FIG. 7, suppression of progesterone in these cells occurred with Troglitazone and this correlated with the increased binding to the DR-1 consensus sequence in EMSA.

EXAMPLE 4

Dose-Response of Human HGL5 Cells Treated with Troglitazone

Figure 8:
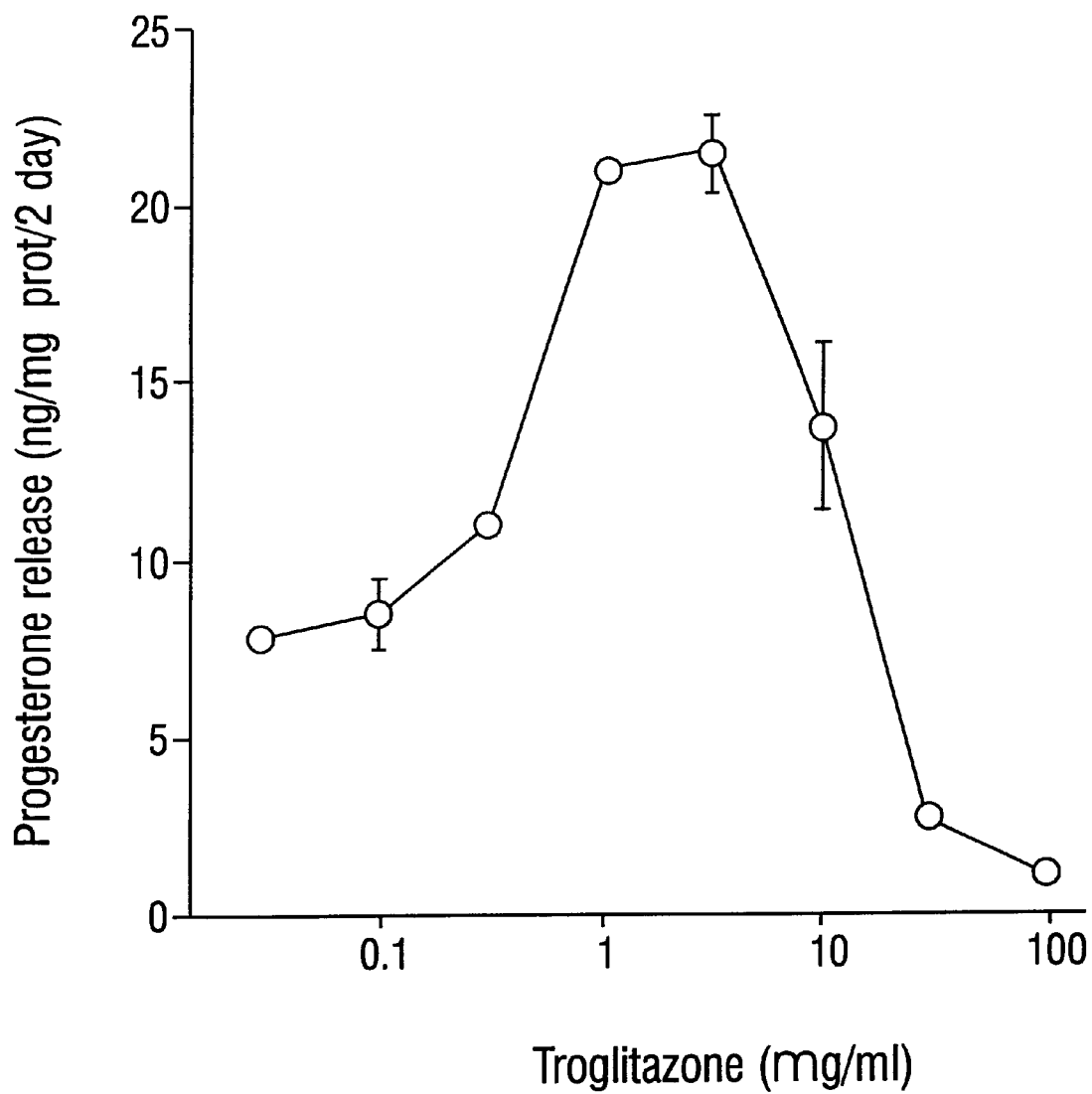
FIG. 8. Dose-response of Troglitazone on progesterone production by HGL5 human granulosa cell line. The human granulosa cell line HGL5 was cultured and treated with Troglitazone in a logarithmic dose-response curve as shown. Cells were treated for 48 h. Progesterone was corrected for protein concentration. The data represent the mean±SEM from 2 studies done in triplicate.

A PPARγ expressing human granulosa cell line (HGL5) was selected that had been transformed by the E6 and E7 regions of the human papillomavirus (Rainey et al., 1994). Although these cells were slow growing in cell culture, they retained their steroidogenic capacity (Rainey et al., 1994). Troglitazone also suppressed progesterone production in this cell line, although the suppression occurred only at concentrations of Troglitazone greater than 10 μg/ml (FIG. 8). Moreover, there was a biphasic response to Troglitazone, with lower concentrations actually increasing progesterone production (FIG. 8).

Figure 10:
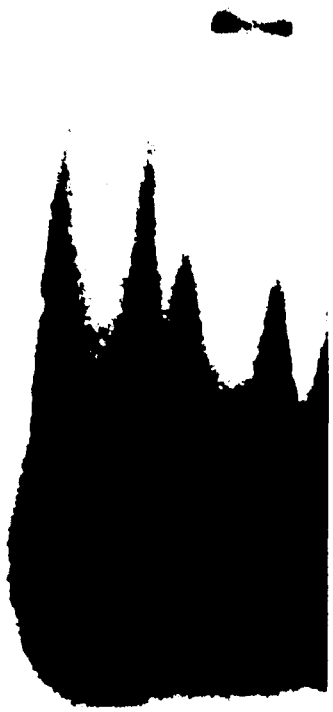
FIG. 10. EMSA of nuclear extract protein from HPL5 cells. HPL5 cells were cultured as control (B) or treated with Troglitazone (30 µg/ml) (T) for 24 h. EMSA was done with 15 µg of protein and radioactively-labeled PPRE consensus oligonucleotide. EMSA conditions are as previously described for porcine granulosa cells.

EMSA was next performed on nuclear extract protein from HGL5 cells to determine whether the increase in binding to the DR-1 consensus sequence induced by Troglitazone in porcine granulosa cells was also present in this cell line. Troglitazone at a 30 μg/ml concentration inhibited progesterone production by these cells and also markedly increased binding to the PPRE (FIG. 10).

Figure 9:
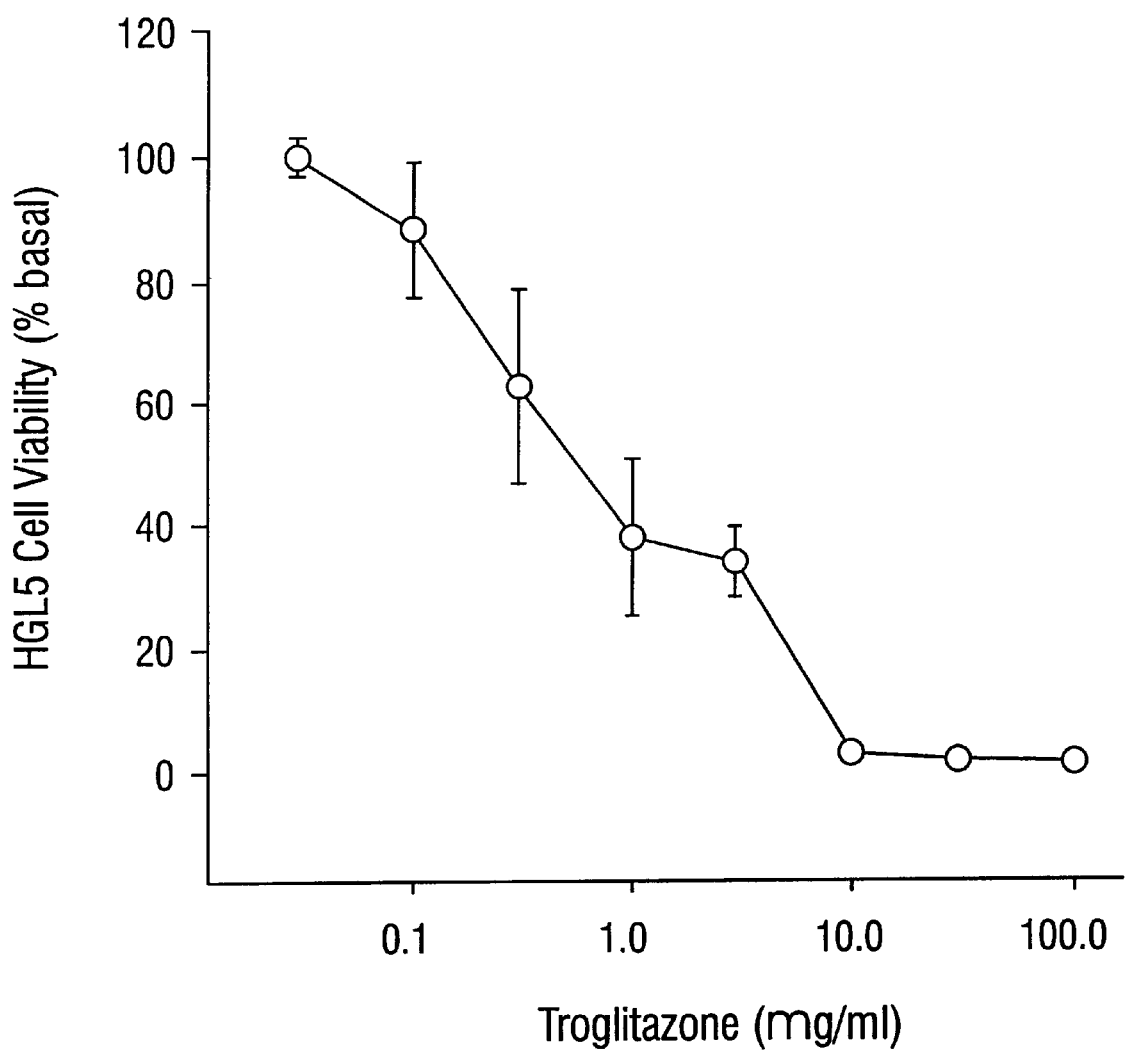
FIG. 9. Cell viability of HGL5 cells treated with Troglitazone. HGL5 cells were treated with increasing concentrations of Troglitazone for 4 days. Cell viability was assessed by the conversion of MTT to formazan as previously described. Data are the mean+SEM from 2 studies done in triplicate.

The effects of Troglitazone on cell viability in the HGL5 cells was next tested. A similar assay was used as described above for porcine granulosa cells, using MTT instead of MTS for conversion to formazan. As shown in FIG. 9, Troglitazone concentrations as low as 0.5 μg/ml caused a loss of cell viability. This demonstrated the utility of Troglitazone in decreasing the viability of this immortal, transformed cell line.

EXAMPLE 5

Figure 11:
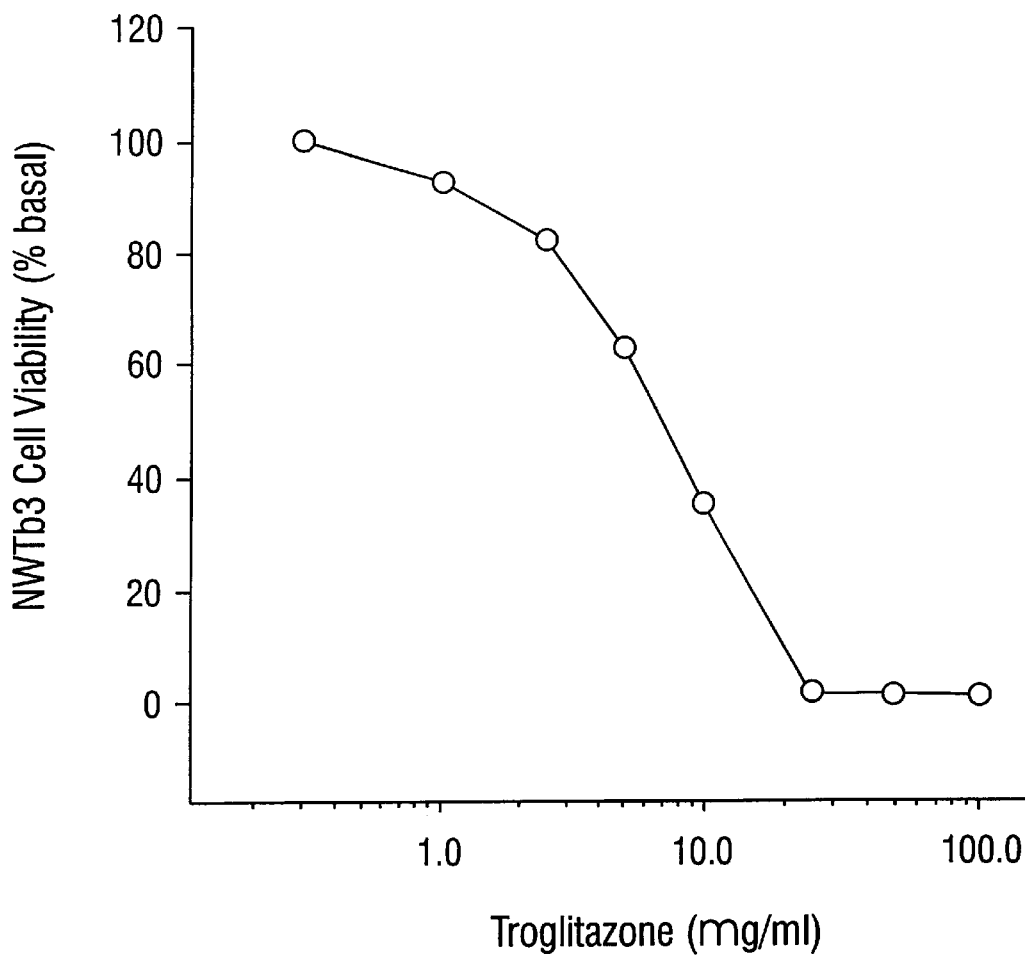
FIG. 11. Cell viability of NWTb3 cells treated with Troglitazone. NWTb3 cells were treated for 4 days with increasing concentrations of Troglitazone. Cells were grown in 24 well-plates with high-glucose MEM/10% FCS. Cell viability was assessed by the conversion of MTT to formazan as previously described. Data are the mean±SEM from 2 studies done in triplicate.

Treatment of Mouse Fibroblast NWTb3 Cells with Troglitazone: Effects on Cell Viability, and Binding to the PPRE Because a decrease in cell viability was observed with the human granulosa cell line (HGL5), the effects of Troglitazone on 2 other cell lines was studied. The first cell line tested with Troglitazone was a PPARγ expressing transformed mouse fibroblast line derived from NIH 3T3 cells which over expresses the IGF-I receptor (NWTb3). These cells are of mesenchymal origin and grow more rapidly than the HGL5 line. In this cell line Troglitazone caused a loss of cell viability at concentrations of 1.0 μg/ml and greater (FIG. 11). These results indicated that Troglitazone is effective in decreasing the viability of PPARγ-expressing transformed cell lines, and further indicate the applicability of Troglitazone in the treatment of tumor cells.

Figure 12:
FIG. 12. EMSA of NWTb3 cells treated with Troglitazone. Nuclear extract protein (25 µg) was used in EMSA as previously described with radioactively-labeled consensus PPRE. C indicates control NWTb3 cells and T indicates NWTb3 cells treated with 10 µg/ml Troglitazone for 24 h.

EMSA was also done on nuclear extract protein from NWTb3 cells treated with 10 μg/ml of Troglitazone to determine whether an increase in binding to the PPRE was seen as in the 2 previous systems (porcine and human granulosa). As shown in FIG. 12, an increase in binding of PPRE was seen during treatment with Troglitazone. This again, suggests that the effects of troglitazone and related thiazolidinedione derivatives are mediated by binding to the DR-1 consensus sequence.

EXAMPLE 6

Effects of Troglitazone on the Viability of Human MCF-7 Cells

Figure 13:
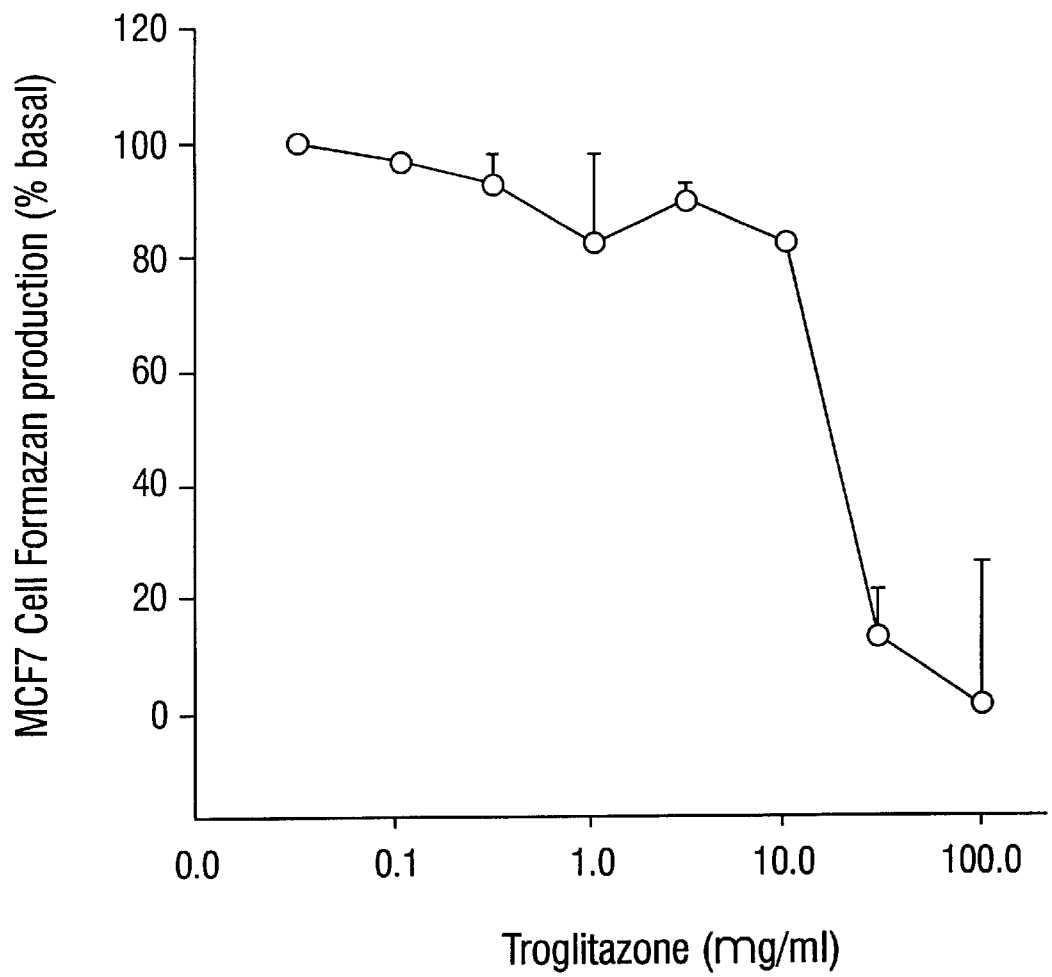
FIG. 13. Cell viability of MCF-7 cells treated with Troglitazone. MCF-7 cells were treated with increasing concentrations of Troglitazone for 4 days and cell viability was assessed by the conversion of MTT to formazan as previously described. Data are the mean±SEM from 2 studies done in triplicate.

A non-PPARγ expressing human breast cancer cell line, MCF-7, was tested. In this cell line, which is nonmesenchymal in origin, cell viability decreased only with high concentrations of Troglitazone (FIG. 13). Nuclear extract protein collected from MCF-7 cells treated with 30 μg/ml of Troglitazone for 24 h and used in EMSA with the DR-1 consensus sequence showed no presence of binding. The results show that loss of cell viability is correlated with the expression of PPARγ in transformed and cancer cells.

REFERENCES

The following references, to the extent that they provide exemplary procedural or other details supplementary to those set forth herein, are specifically incorporated herein by reference.

Barentsen R, Eur J Obs Gyn & Repr Biol 64 Suppl:s7–11, 1996.

Berge et al., "Pharmaceutical Salts," *J Pharm. Science*, 66:1–19, 1977.

Connelly EF, Budd GT, Seminars in Oncology 23:16–21, 1996.

Dunaif, Scott, Finegood, Quintana, Whitcomb, "The insulin-sensitizing agent Troglitazone improves metabolic and reproductive abnormalities in the polycystic ovary syndrome," *J Clin. Endocrinol. Metab.*, 81:3299–3306, 1996.

Forman, Tontonoz, Chen, Brun, Spiegelman, Evans, "15-Deoxy-delta$^{12, 14}$-Prostaglandin J$_2$ is a ligand for the adipocyte determination factor PPAR gamma," *Cell*, 83:803–812, 1995.

Kliewer, Lenhard, Wilson, Patel, Morris, Lehman, "A prostaglandin J$_2$ metabolite binds peroxisome proliferator-activated receptor gamma and promotes adipocyte differentiation," *Cell.*, 83:813–819, 1995.

Lehmann, Moore, Smith-Oliver, Wilkison, Willson, Kliewer, "An antidiabetic thiazolidinedione is a high affinity ligand for peroxisome proliferator-activated receptor gamma (PPARgamma)," *J. Biol. Chem.*, 270:12953–12956, 1995.

Marcus, Capone, Rachubinski, "Identification of COUP-TFII as a peroxisome proliferator response element binding factor using genetic selection in yeast: COUP-TFII activates transcription in yeast but antagonizes PPAR signaling in mammalian cell," *Mol. Cell. Endocrinol.*, 120:31–39, 1996.

Miller, "Molecular biology of steroid hormone synthesis," *Endocr. Rev.*, 9:295–318, 1988.

Motojima, "Peroxisome proliferator-activated receptor (PPAR): Structure, mechanisms of activation and diverse functions," *Cell Structure and Function*, 18:267–277, 1993.

Nolan, Ludvik, Beerdsen, Joyce, Olefsky, "Improvement in glucose tolerance and insulin resistance in obese subjects treated with Troglitazone," *N. Engl. J. Med.*, 331:1188–1193, 1994.

Odell PF, Journal of Otolaryngology 25:7–13, 1996.

Pierce WC, Figlin RA, Curr Opin Oncology 5:343–352, 1992.

Raincy, Sawetawan, Shay, Michael, Mathis, Kutteh, Byrd, Carr, "Transformation of human granulosa cells with the E6 and E7 regions of human papillomavirus," *J. Clin. Endocrinol. Metabl.*, 78:705–710, 1994.

Shaaban MM, "The perimenopause and contratception" Maturitas 23:181–192, 1996.

Urban, Bodenburg, Nagamani, Peirce, "Dexamethasone potentiates IGF-I actions in porcine granulosa cells," *Am. J. Physiol.*, 267:E115-E123, 1994.

Urban, Garney, Shupnik, Veldhuis, "Insulin-like growth factor type I increases concentrations of messenger RNA encoding cytochrome P450 cholesterol side chain cleavage enzyme in primary cultures of porcine granulosa cells," *Endocrinology*, 127:2481–2488, 1990.

Veldhuis and Furlanette, "Trophic actions of human somatomedin C/insulin-like growth factor I on ovarian cells: in vitro studies with swine granulosa cells," *Endocrinology*, 116:1235–1242, 1985.

Vidal-Puig, Jimenez, Liñan, Lowell, Hamann, Hu, Spiegelman, Flier, Moller, "Regulation of PPAR gamma gene expression by nutrition and obesity in rodents," *J. Clin. Invest.*, 97:2553–2561, 1996.

---

---

What is claimed is:

1. A method for treating a tumor in a subject comprising administering a therapeutically effective amount of a compound of Formula I:

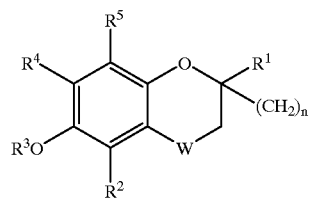

Formula I

-continued

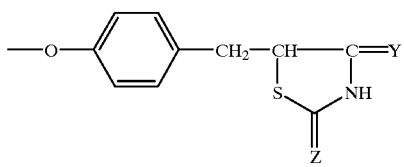

wherein R¹ and R² are the same or different and each represents a hydrogen atom or a $C_1$–$C_5$ alkyl group;

R³ represents a hydrogen atom, a $C_1$–$C_6$ aliphatic acyl group, an alicyclic acyl group, an aromatic acyl group, a heterocyclic acyl group, an araliphatic acyl group, a ($C_1$–$C_6$ alkoxy)carbonyl group, or an aralkyloxycarbonyl group;

R⁴ and R⁵ are the same or different and each represents a hydrogen atom, a $C_1$–$C_5$ alkyl group or a $C_1$–$C_5$ alkoxy group, or R⁴ and R⁵ together represent a $C_1$–$C_4$ alkylenedioxy group;

n is 1, 2 or 3;

W represents the —$CH_2$—,>CO, or CH—OR⁶ group (in which R⁶ represents any one of the atoms or groups defined for R³ and may be the same as or different from R³); and Y and Z are the same or different and each represents an oxygen atom or an imino (=NH) group; and pharmaceutically acceptable salts thereof.

2. A method of treating a tumor in a subject, comprising administering a therapeutically effective amount of a compound according to claim 1 in admixture with a pharmaceutically acceptable excipient, diluent, or carrier.

3. The method of claim 1 wherein Y and Z are oxygen.

4. The method of claim 1 wherein W is —$CH_2$—.

5. The method of claim 1 wherein n is 1.

6. The method of claim 1 wherein R¹, R², R⁴, and R⁵ are lower alkyl and R³ is H.

7. The method of claim 1 wherein Z and Y are oxygen, n is 1, and W is —$CH_2$—.

8. The method of claim 1 wherein the compound is (+)-5-[[4-[(3,4-dihydro-6-hydroxy-2,5,7,8-tetramethyl-2H-1-benzopyran-2-yl) methoxy]phenyl]methyl]-2,4-thiazolidinedione.

9. The method of claim 1, wherein said treatment comprises administration of about 400 mg per day of a compound of formula I.

10. A method of treating a tumor in a subject, comprising the administration to a host suffering therefrom a therapeutically effective amount of a compound of Formula II:

Formula II

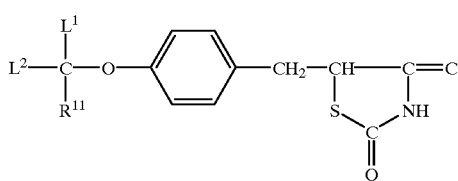

wherein R¹¹ is substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula

wherein R¹³ and R¹⁴ are the same or different and each is lower alkyl or R¹³ and R¹⁴ are combined to each other either directly or as interrupted by a heteroatom selected from the group consisting of nitrogen, oxygen, and sulfur to form a 5- or 6- membered ring;

wherein R¹² means a bond or lower alkylene group; and wherein L¹ and L² are the same or different and each is hydrogen or lower alkyl or L¹ and L² are combined to form an alkylene group; or a pharmaceutically acceptable salt thereof.

11. The method of claim 10 wherein the compound is in admixture with a pharmaceutically acceptable excipient, diluent, or carrier.

12. The method of claim 10 wherein the compound is troglitazone.

13. The method of claim 10 wherein the compound is pioglitazone.

14. The method of claim 10 wherein the compound is BRL 49653.

15. The method of claim 10 wherein the tumor comprises a messenchymal tumor.

16. A method of treating a tumor in a subject comprising administering to a host suffering therefrom a therapeutically effective amount of a compound of Formula III:

Formula III

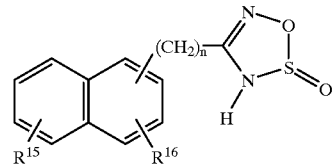

wherein R¹⁵ and R¹⁶ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4 and the pharmaceutically acceptable salts thereof.

17. A method of treating a tumor in a subject comprising administering to a host suffering therefrom a therapeutically effective amount of a compound of Formula IV:

Formula IV

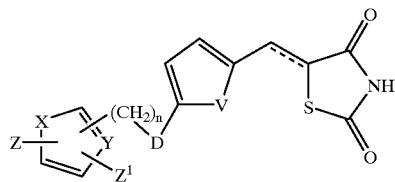

wherein the dotted line represents a bond or no bond;

V is —CH=CH—, —N=CH—, —CH=N— or S;

D is $CH_2$, CHOH, CO, C=NOR₁₇ or CH=CH;

X is S, O, NR₁₈, —CH=N or —N=CH

Y is CH or N;

Z is hydrogen, ($C_1$–$C_7$)alkyl, ($C_3$–$C_7$)cycloalkyl, phenyl, naphthyl, pyridyl, furyl, thienyl, or phenyl mono- or disubstituted with the same or different groups which are (C$_3$–C$_3$)alkyl, trifluoromethyl, (C$_1$–C$_3$)alkoxy, fluoro, chloro, or bromo;

Z$^1$ is hydrogen or (C$_1$–C$_3$)alkyl;

R$^{17}$ and R$^{18}$ are each independently hydrogen or methyl; and n is 1, 2, or 3;

the pharmaceutically acceptable cationic salts thereof; and the pharmaceutically acceptable acid addition salts thereof when the compound contains a basic nitrogen.

18. A method of treating a tumor in a subject comprising administering to a host suffering therefrom a therapeutically effective amount of a compound of Formula V:

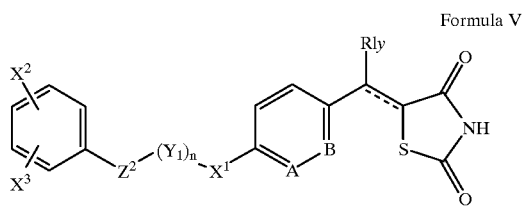

Formula V wherein the dotted line represents a bond or no bond;

A and B are each independently CH or N, with the proviso that when A or B is N, the other is CH;

X$^1$ is S, SO, SO$_2$, CH$_2$, CHOH, or CO;

n is 0 or 1;

Y$^1$ is CHR$_{20}$ or R$^{21}$, with the proviso that when n is 1 and Y$^1$ is NR$_{21}$, X$^1$ is SO$_2$ or CO;

Z$^2$ is CHR$_{22}$, CH$_2$CH$_2$, CH=CH,

OCH$_2$, SCH$_2$, SOCH$_2$ or SO$_2$CH$_2$;

R$^{19}$, R$^{20}$, R$^{21}$, and R$^{22}$ are each independently hydrogen or methyl; and X$^2$ and X$^3$ are each independently hydrogen, methyl, trifluoromethyl, phenyl, benzyl, hydroxy, methoxy, phenoxy, benzyloxy, bromo, chloro, or fluoro;

a pharmaceutically acceptable cationic salt thereof; or a pharmaceutically acceptable acid addition salt thereof when A or B is N.

19. A method of treating a tumor in a subject comprising administering to a host suffering therefrom a therapeutically effective amount of a compound of Formula VI:

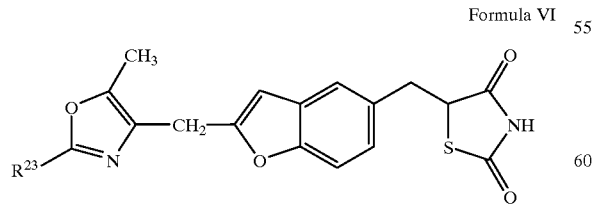

Formula VI or a pharmaceutically acceptable salt thereof wherein R$^{23}$ is alkyl of 1 to 6 carbon atoms, cycloalkyl of 3 to 7 carbon atoms, phenyl or mono- or disubstituted phenyl wherein said substituents are independently alkyl of 1 to 6 carbon atoms, alkoxy of 1 to 3 carbon atoms, halogen, or trifluoromethyl.

20. A method of treating a tumor in a subject comprising administering to a host suffering therefrom a therapeutically effective amount of a compound of Formula VII:

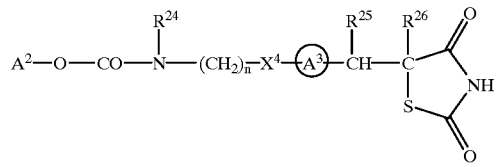

Formula VII or a tautomeric form thereof and/or a pharmaceutically acceptable salt thereof, and/or a pharmaceutically acceptable solvate thereof, wherein:

A$^2$ represents an alkyl group, a substituted or unsubstituted aryl group, or an aralkyl group wherein the alkylene or the aryl moiety may be substituted or unsubstituted;

A$^3$ represents a benzene ring having in total up to 3 optional substituents;

R$^{24}$ represents a hydrogen atom, an alkyl group, an acyl group, an aralkyl group wherein the alkyl or the aryl moiety may be substituted or unsubstituted, or a substituted or unsubstituted aryl group; or A$^2$ together with R$^{24}$ represents substituted or unsubstituted C$_{2-3}$ polymethylene group, optional substituents for the polymethylene group being selected from alkyl or aryl or adjacent substituents together with the methylene carbon atoms to which they are attached form a substituted or unsubstituted phenylene group;

R$^{25}$ and R$^{26}$ each represent hydrogen, or R$^{25}$ and R$^{26}$ together represent a bond;

X$^4$ represents O or S; and n represents an integer in the range from 2 to 6.

21. A method of treating a tumor in a subject comprising administering to a host suffering therefrom a therapeutically effective amount of a compound of Formula VIII in unit dosage form:

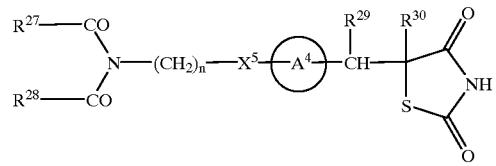

Formula VIII or a tautomeric form thereof and/or a pharmaceutically acceptable salt thereof, and/or a pharmaceutically acceptable solvate thereof, wherein:

R$^{27}$ and R$^{28}$ each independently represent an alkyl group, a substituted or unsubstituted aryl group, or an aralkyl group being substituted or unsubstituted in the aryl or alkyl moiety; or R$^{27}$ together with R$^{28}$ represents a linking group, the linking group consisting of an optionally substituted methylene group or an O or S atom, optional substituents for the said methylene groups being selected from alkyl-, aryl, or aralkyl, or substituents of adjacent methylene groups together with the carbon atoms to which they are attached form a substituted or unsubstituted phenylene group;

$R^{29}$ and $R^{30}$ each represent hydrogen, or $R^{29}$ and $R^{30}$ together represent a bond;

$A^4$ represents a benzene ring having in total up to 3 optional substituents;

$X^5$ represents O or S; and n represents an integer in the range from 2 to 6.

22. A method of treating a tumor in a subject comprising administering to a host suffering therefrom a therapeutically effective amount of a compound of Formula IX:

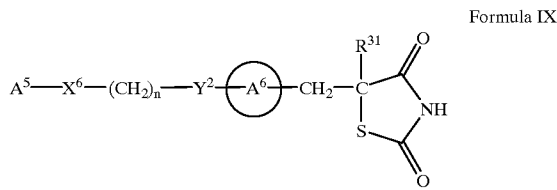

Formula IX or a tautomeric form thereof and/or a pharmaceutically acceptable salt thereof, and/or a pharmaceutically acceptable solvate thereof, wherein:

$A^5$ represents a substituted or unsubstituted aromatic heterocyclyl group;

$A^6$ represents a benzene ring having in total up to 5 substituents;

$X^6$ represents O, S, or $NR_{32}$ wherein $R^{32}$ represents a hydrogen atom, an alkyl group, an acyl group, an aralkyl group, wherein the aryl moiety may be substituted or unsubstituted, or a substituted or unsubstituted aryl group;

$Y^2$ represents O or S;

$R^{31}$ represents an alkyl, aralkyl, or aryl group; and n represents an integer in the range from 2 to 6.

23. A method of treating a tumor in a subject comprising administering to a host suffering therefrom a therapeutically effective amount of a compound of Formula X:

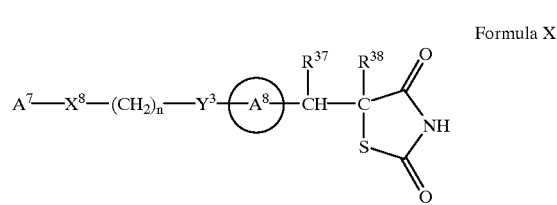

Formula X or a tautomeric form thereof and/or a pharmaceutically acceptable salt thereof, and/or a pharmaceutically acceptable solvate thereof, wherein:

$A^7$ represents a substituted or unsubstituted aryl group;

$A^8$ represents a benzene ring having in total up to 5 substituents;

$X^8$ represents O, S, or $NR_{39}$ wherein $R^{39}$ represents a hydrogen atom, an alkyl group, an acyl group, an aralkyl group, wherein the aryl moiety may be substituted or unsubstituted, or a substituted or unsubstituted aryl group;

$Y^3$ represents O or S;

$R^{37}$ represents hydrogen;

$R^{38}$ represents hydrogen or an alkyl, aralkyl, or aryl group or $R^{37}$ together with $R^{38}$ represents a bond; and n represents an integer in the range from 2 to 6.

24. A method of treating a tumor in a subject comprising administering to a host suffering therefrom a therapeutically effective amount of a compound of Formula XI:

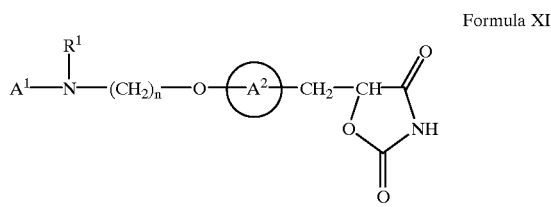

Formula XI or a tautomeric form thereof and/or a pharmaceutically acceptable salt thereof, and/or a pharmaceutically acceptable solvate thereof, wherein:

$A^1$ represents a substituted or unsubstituted heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to 5 substituents; and n represents an integer in the range of from 2 to 6.

25. A method of treating a tumor in a subject comprising administering to a host suffering therefrom a therapeutically effective amount of a compound of Formula XII or XIII:

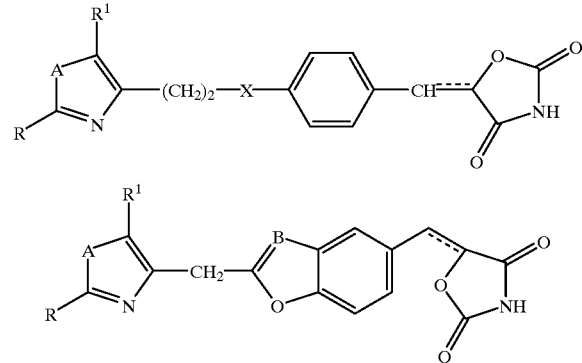

Formulas XII and XIII or a pharmaceutically acceptable salt thereof wherein the dotted line represents a bond or no bond;

R is cycloalkyl of three to seven carbon atoms, naphthyl, thienyl, furyl, phenyl or substituted phenyl wherein said substituent is alkyl of one to three carbon atoms, alkoxy of one to three carbon atoms, trifluoromethyl, chloro, fluoro or bis(trifluoromethyl);

$R^1$ is alkyl of one to three carbon atoms;

X is O or C=O;

A is O or S; and

B is N or CH.

26. A method of treating a tumor in a subject comprising administering to a host suffering therefrom a therapeutically effective amount of a compound selected from the group consisting of (+)-5-[[4-[(3,4-dihydro-6-hydroxy-2,5,7,8-tetramethyl-2H-1-benzopyran-2-yl) methoxy]phenyl]methyl]-2,4-thiazolidinedione: (troglitazone);

4-(2-naphthylmethyl)-1,2,3,5-oxathiadiazole-2-oxide;

5-[4-[2-[N-(benzoxazol-2-yl)-N-methylamino]ethoxy]
benzyl]-5-methylthiazolidine-2,4-dione;

5-[4-[2-[2,4-dioxo-5-phenylthiazolidin-3-yl)ethoxy]
benzyl]thiazolidine-2,4-dione;

5-[4-[2-[N-methyl-N-(phenoxycarbonyl)amino]ethoxy]
benzyl]thiazolidine-2,4-dione;

5-[4-(2-phenoxyethoxy)benzyl]thiazolidine-2,4-dione;

5-[4-[2-(4-chlorophenyl)ethylsulfonyl]benzyl]
thiazolidine-2,4-dione;

5-[4-[3-(5-methyl-2-phenyloxazol-4-yl)propionyl]
benzyl]thiazolidine-2,4-dione;

5-[4-[(1-methylcyclohexyl)methoxy]benzyl]
thiadiazolidine-2,4-dione: (ciglitazone);

5-[[4-(3-hydroxy-1-methylcyclohexyl)methoxy]benzyl]
thiadiazolidine-2,4-dione;

5-[4-[2-(5-methyl-2-phenyloxazol-4-yl)ethoxyl]benzyl]
thiadizolidione-2,4-dione;

5-[4-[2-(5-ethylpyridin-2-yl)ethoxyl]benzyl]
thiadiazolidine-2,4-dione: (pioglitazone);

5-[(2-benzyl-2,3-dihydrobenzopyran)-5-ylmethyl]
thiadiazoline-2,4-dione: (englitazone);

5-[[2-(2-naphthylmethyl)benzoxazol]-5-ylmethyl]
thiadiazoline-2,4-dione;

5-[4-[2-(3-phenylureido)ethoxyl]benzyl]thiadiazoline-2,
4-dione;

5-[4-[2-[N-(benzoxazol-2-yl)-N-methylamino]ethoxy]
benzy]thiadiazoline-2,4-dione;

5-[4-[3-(5-methyl-2-phenyloxazol-4-yl)propionyl]
benzyl]thiadiazoline-2,4-dione;

5-[2-(5-methyl-2-phenyloxazol-4-ylmethyl)benzofuran-
5-ylmethyl]-oxazolidine -2,4-dione;

5-[4-[2-[N-methyl-N-(2-pyridyl)amino]ethoxy]benzyl]
thiazolidine-2,4-dione (BRL49653); and 5-[4-[2-[N-(benzoxazol-2-yl)-N-methylamino]ethoxy]
benzyl]-oxazolidine-2,4-dione.

* * * * *

UNITED STATES PATENT AND TRADEMARK OFFICE
CERTIFICATE OF CORRECTION

PATENT NO. : 6,207,690 B1
DATED : March 27, 2001
INVENTOR(S) : Urban et al.

It is certified that error appears in the above-identified patent and that said Letters Patent is hereby corrected as shown below:

<u>Title page,</u>
Item [63], delete "Pat. No. 5,814,674" and insert -- Pat. No. 5,814,647 -- therefor.

Signed and Sealed this

Twenty-eighth Day of May, 2002

Attest:

JAMES E. ROGAN
Attesting Officer    Director of the United States Patent and Trademark Office

SEQUENCE LISTING

```
<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<221> NAME/KEY: modified_base
<222> LOCATION: (1)..(10)
<223> OTHER INFORMATION: N = A or G or C or T
<220> FEATURE:
<223> OTHER INFORMATION: Description of Artificial Sequence: Synthetic
      Primer

<400> SEQUENCE: 1
nnnaggtcan aggtca                                                     16
```